(12) United States Patent
Lau et al.

(10) Patent No.: US 8,052,604 B2
(45) Date of Patent: Nov. 8, 2011

(54) METHODS AND APPARATUS FOR ENGAGEMENT AND COUPLING OF AN INTRACAVITORY IMAGING AND HIGH INTENSITY FOCUSED ULTRASOUND PROBE

(75) Inventors: Michael P. H. Lau, Edmonds, WA (US); Gregory Paul Darlington, Snohomish, WA (US); Michael J. Connolly, Bothell, WA (US); Zihong Guo, Bellevue, WA (US)

(73) Assignee: Mirabilis Medica Inc., Bothell, WA (US)

( * ) Notice: Subject to any disclaimer, the term of this patent is extended or adjusted under 35 U.S.C. 154(b) by 699 days.

(21) Appl. No.: 11/831,048

(22) Filed: Jul. 31, 2007

(65) Prior Publication Data

US 2009/0036773 A1     Feb. 5, 2009

(51) Int. Cl.
*A61B 8/00* (2006.01)
*A61B 8/14* (2006.01)

(52) U.S. Cl. .................. 600/439; 600/459; 600/462

(58) Field of Classification Search .................. 600/439, 600/459–467
See application file for complete search history.

(56) References Cited

U.S. PATENT DOCUMENTS

| | | |
|---|---|---|
| 3,470,868 A | 10/1969 | Krause |
| 3,480,002 A | 11/1969 | Flaherty |
| 3,676,584 A | 7/1972 | Plakas |
| 3,941,112 A | 3/1976 | Habert |
| 4,059,098 A | 11/1977 | Murdock |
| 4,097,835 A | 6/1978 | Green |
| 4,185,502 A | 1/1980 | Frank |
| 4,282,755 A | 8/1981 | Gardineer et al. |
| 4,347,850 A | 9/1982 | Kelly-Fry |
| 4,484,569 A | 11/1984 | Driller |

(Continued)

FOREIGN PATENT DOCUMENTS

EP    0301360 B1    2/1989
(Continued)

OTHER PUBLICATIONS

Cain, C.A., and S.-I. Umemura, "Concentric-Ring and Sector-Vortex Phased-Array Applicators for Ultrasound Hyperthermia," IEEE Transactions on Microwave Theory and Techniques 34(5):542-551, May 1986.

(Continued)

*Primary Examiner* — Long V Le
*Assistant Examiner* — Angela M Hoffa
(74) *Attorney, Agent, or Firm* — Christensen O'Connor Johnson Kindness PLLC

(57) ABSTRACT

A combined imaging/HIFU probe includes an imaging scan head, a HIFU transducer, and an outlet port that delivers a flow of fluid across the HIFU transducer. At least a portion of the body cavity is filled with fluid in which the probe is immersed. The fluid provides a coupling for transmission of ultrasound energy between the probe and the patient. A flow of fluid may also be used to flush obstructions from an area of tissue near the HIFU transducer. Further described herein is a cuff to help retain fluid in the body cavity, a regulator to regulate fluid flow with respect to the body cavity according to a desired fluid pressure, and a cover for the HIFU transducer that has at least one perforation defined therethrough to allow fluid to flow through the cover. Further disclosed herein are methods of deploying a combined imaging/HIFU probe in a body cavity.

49 Claims, 9 Drawing Sheets

U.S. PATENT DOCUMENTS

| | | | |
|---|---|---|---|
| 4,742,829 A | 5/1988 | Law | |
| 4,756,313 A * | 7/1988 | Terwilliger | 600/462 |
| 4,835,689 A | 5/1989 | O'Donnell | |
| 4,858,613 A | 8/1989 | Fry | |
| 4,865,042 A | 9/1989 | Umemura | |
| 4,893,624 A | 1/1990 | Lele | |
| 5,005,579 A | 4/1991 | Wurster | |
| 5,036,855 A | 8/1991 | Fry | |
| 5,080,101 A | 1/1992 | Dory | |
| 5,080,102 A | 1/1992 | Dory | |
| 5,080,660 A | 1/1992 | Buelna | |
| 5,117,832 A | 6/1992 | Sanghvi | |
| 5,234,429 A | 8/1993 | Goldhaber | |
| 5,271,402 A * | 12/1993 | Yeung et al. | 600/437 |
| 5,391,140 A | 2/1995 | Schaetzle | |
| 5,441,499 A | 8/1995 | Fritzsch | |
| 5,471,988 A | 12/1995 | Fujio | |
| 5,474,071 A | 12/1995 | Chapelon | |
| 5,492,126 A | 2/1996 | Hennige | |
| 5,520,188 A | 5/1996 | Hennige | |
| 5,558,092 A | 9/1996 | Unger | |
| 5,619,999 A | 4/1997 | Von Behren | |
| 5,666,954 A | 9/1997 | Chapelon | |
| 5,720,287 A | 2/1998 | Chapelon | |
| 5,762,066 A | 6/1998 | Law | |
| 5,769,790 A | 6/1998 | Watkins | |
| 5,810,007 A | 9/1998 | Holupka | |
| 5,882,302 A | 3/1999 | Driscoll, Jr. | |
| 5,976,092 A | 11/1999 | Chinn | |
| 5,993,389 A | 11/1999 | Driscoll, Jr. | |
| 6,002,251 A | 12/1999 | Sun | |
| 6,007,499 A | 12/1999 | Martin | |
| 6,042,556 A | 3/2000 | Beach | |
| 6,050,943 A | 4/2000 | Slayton | |
| 6,083,159 A | 7/2000 | Driscoll, Jr. | |
| 6,126,607 A * | 10/2000 | Whitmore et al. | 600/459 |
| 6,196,972 B1 | 3/2001 | Moehring | |
| 6,217,530 B1 | 4/2001 | Martin | |
| 6,254,601 B1 | 7/2001 | Burbank | |
| 6,267,734 B1 | 7/2001 | Ishibashi | |
| 6,315,741 B1 | 11/2001 | Martin | |
| 6,390,973 B1 | 5/2002 | Ouchi | |
| 6,425,867 B1 | 7/2002 | Vaezy | |
| 6,432,067 B1 | 8/2002 | Martin | |
| 6,451,013 B1 | 9/2002 | Bays | |
| 6,461,314 B1 | 10/2002 | Pant | |
| 6,488,639 B1 | 12/2002 | Ribault | |
| 6,500,133 B2 | 12/2002 | Martin | |
| 6,537,224 B2 | 3/2003 | Mauchamp | |
| 6,602,251 B2 | 8/2003 | Burbank | |
| 6,613,004 B1 | 9/2003 | Vitek | |
| 6,626,855 B1 | 9/2003 | Weng | |
| 6,633,658 B1 | 10/2003 | Dabney | |
| 6,645,162 B2 | 11/2003 | Friedman | |
| 6,666,835 B2 | 12/2003 | Martin | |
| 6,676,601 B1 | 1/2004 | Lacoste | |
| 6,692,450 B1 | 2/2004 | Coleman | |
| 6,716,184 B2 | 4/2004 | Vaezy | |
| 6,719,694 B2 | 4/2004 | Weng | |
| 6,740,082 B2 | 5/2004 | Shadduck | |
| 6,764,488 B1 | 7/2004 | Burbank | |
| 6,840,936 B2 | 1/2005 | Sliwa, Jr. | |
| 6,936,046 B2 | 8/2005 | Hissong | |
| 7,063,666 B2 | 6/2006 | Weng | |
| 7,105,007 B2 | 9/2006 | Hibler | |
| 7,175,596 B2 | 2/2007 | Vitek | |
| 7,258,674 B2 | 8/2007 | Cribbs | |
| 7,452,357 B2 | 11/2008 | Voegele | |
| 7,470,241 B2 | 12/2008 | Weng | |
| 7,473,224 B2 | 1/2009 | Makin | |
| 7,699,782 B2 * | 4/2010 | Angelsen et al. | 600/444 |
| 2001/0012934 A1 | 8/2001 | Chandrasekaran | |
| 2002/0029036 A1 | 3/2002 | Goble | |
| 2002/0065512 A1 | 5/2002 | Fjield | |
| 2002/0120259 A1 | 8/2002 | Lettice | |
| 2003/0004439 A1 | 1/2003 | Pant | |
| 2003/0060736 A1 | 3/2003 | Martin | |
| 2003/0233045 A1 | 12/2003 | Vaezy | |
| 2004/0030269 A1 | 2/2004 | Horn | |
| 2004/0082859 A1 | 4/2004 | Schaer | |
| 2004/0153126 A1 | 8/2004 | Okai | |
| 2004/0242999 A1 | 12/2004 | Vitek | |
| 2004/0243201 A1 | 12/2004 | Goldman | |
| 2005/0038340 A1 | 2/2005 | Vaezy | |
| 2005/0085726 A1 | 4/2005 | Lacoste | |
| 2005/0101854 A1 | 5/2005 | Larson | |
| 2005/0154431 A1 | 7/2005 | Quistgaard | |
| 2005/0203399 A1 | 9/2005 | Vaezy | |
| 2005/0256405 A1 | 11/2005 | Makin | |
| 2005/0267454 A1 | 12/2005 | Hissong | |
| 2006/0052701 A1 | 3/2006 | Carter | |
| 2006/0264748 A1 | 11/2006 | Vaezy | |
| 2007/0066990 A1 | 3/2007 | Marsella | |
| 2007/0194658 A1 | 8/2007 | Zhang | |
| 2007/0197918 A1 | 8/2007 | Vitek | |
| 2007/0238994 A1 | 10/2007 | Stecco | |
| 2008/0039724 A1 | 2/2008 | Seip | |
| 2008/0071165 A1 | 3/2008 | Makin | |
| 2008/0086036 A1 | 4/2008 | Hartley | |
| 2008/0125771 A1 | 5/2008 | Lau | |
| 2008/0221647 A1 | 9/2008 | Chamberland | |
| 2008/0281314 A1 | 11/2008 | Johnson | |
| 2008/0319436 A1 | 12/2008 | Daniel | |
| 2009/0036774 A1 | 2/2009 | Weng | |
| 2009/0228001 A1 | 9/2009 | Pacey | |
| 2009/0326420 A1 | 12/2009 | Moonen | |

FOREIGN PATENT DOCUMENTS

| | | | |
|---|---|---|---|
| EP | 0614651 A1 | | 9/1994 |
| EP | 0734742 A2 | | 10/1996 |
| EP | 1 726 267 A2 | | 11/2006 |
| JP | 05023336 A | * | 2/1993 |
| WO | 93/17646 A2 | | 9/1993 |
| WO | WO 9427502 A1 | * | 12/1994 |
| WO | 95/20360 A1 | | 8/1995 |
| WO | 97/00646 A1 | | 1/1997 |
| WO | 01/71380 A2 | | 9/2001 |
| WO | 2004/073524 A1 | | 9/2004 |
| WO | 2005/000097 A2 | | 1/2005 |
| WO | 2006097661 A1 | | 9/2006 |

OTHER PUBLICATIONS

Chapelon, J.Y., et al., "The Feasibility of Tissue Ablation Using High Intensity Electronically Focused Ultrasound," Proceedings of the IEEE Ultrasonics Symposium 1993, Baltimore, Oct. 31-Nov. 3, 1993, pp. 1211-1214.

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Coad, J.E., "Thermal Fixation: A Central Outcome of Hyperthermic Therapies," Proceedings of the SPIE Conference on Themal Treatment of Tissue: Energy Delivery and Assessment III 5698:15-22, San Jose, Calif., Jan. 23, 2005.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

Hallberg, L., et al., "Menstrual Blood Loss—A Population Study: Variation at Different Ages and Attempts to Define Normality," Acta Obstetricia et Gynecologica Scandinavica 45(3):320-351, 1966.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Orsini-Meinhard, K., "UW Tech-Transfer Program Putting Discoveries to Work," The Seattle Times, May 27, 2007, 8 pages.

Rabkin, B.A., et al., "Biological and Physical Mechanisms of HIFU-Induced Hyperecho in Ultrasound Images," Ultrasound in Medicine & Biology 32(11):1721-1729, Nov. 2006.

Sanghvi, N.T., et al., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.

"ThermoDox™ Animal Studies to Be Presented at 6th International Symposium on Therapeutic Ultrasound in Oxford, England," Aug. 30-Sep. 2, 2006, Celsion, Inc., <http://www.celsion.com/news/releasedetail.cfm> [retrieved Oct. 8, 2007], 2 pages.

"ThermoDox™ : Heat-Activated Liposome Drug," © 2007 Celsion, Inc., <http://www.celsion.com/products/ThermoDox.cfm> [retrieved Oct. 8, 2007], 3 pages.

Vaezy, S., et al., "Image-Guided Acoustic Therapy," Annual Review of Biomedical Engineering 3:375-390, Aug. 2001.

Winter, T.C., et al., "Focal Tumor Ablation: A New Era in Cancer Therapy," Ultrasound Quarterly 22(3):204-209, Sep. 2006.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5, Pt. I):953-1081, May 1995.

International Search Report dated Jun. 26, 2009, in International Application No. PCT/US2008/082829, filed Nov. 7, 2008.

Daum, D.R., and K. Hynynen, "A 256-Element Ultrasonic Phased Array System for the Treatment of Large Volumes of Deep Seated Tissue," IEEE Transactions on Ultrasonics, Ferroelectrics, and Frequency Control 46(5):1254-1268, Sep. 1999.

Enholm, J.K., et al., "Improved Volumetric MR-HIFU Ablation by Robust Binary Feedback Control," IEEE Transactions on Biomedical Engineering 57(1):103-113, Jan. 2010.

Mougenot, C., et al., "Automatic Spatial and Temporal Temperature Control for MR-Guided Focused Ultrasound Using Fast 3D MR Thermometry and Multispiral Trajectory of the Focal Point, " Magnetic Resonance in Medicine 52:1005-1015, 2004.

Mougenot, C., et al., "Three-Dimensional Spatial and Temporal Temperature Control With MR Thermometry-Guided Focused Ultrasound (MRgHIFU)," Magnetic Resonance in Medicine 61:603-614, 2009.

Ngo, F.C., et al., "An Experimental Analysis of a Sector-Vortex Phased Array Prototype," Proceedings of the IEEE Ultrasonics Symposium, Montreal, Oct. 3-6, 1989, vol. 2, pp. 999-1002.

Rabkin, B.A., et al., "Hyperecho in Ultrasound Images of HIFU Therapy: Involvement of Cavitation," Ultrasound in Medicine and Biology 31(7):947-956, Jul. 2005.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.

Extended European Search Report mailed Feb. 26, 2010, issued in European Patent Application No. 07811847.8, filed Apr. 13, 2007, 7 pages.

International Search Report mailed May 11, 2010, issued in International Application No. PCT/US2009/059589, filed Oct. 5, 2009, 5 pages.

International Search Report and Written Opinion mailed May 18, 2010, issued in International Application No. PCT/US2009/053050, filed Aug. 6, 2009, 15 pages.

International Search Report and Written Opinion mailed Oct. 26, 2010, issued in International Application No. PCT/US2010/026565, filed Mar. 8, 2010, 10 pages.

* cited by examiner

METHODS AND APPARATUS FOR ENGAGEMENT AND COUPLING OF AN INTRACAVITORY IMAGING AND HIGH INTENSITY FOCUSED ULTRASOUND PROBE

FIELD OF THE INVENTION

The present application is directed to methods and apparatus that provide ultrasound imaging and therapeutic treatment of internal pathological conditions using high intensity focused ultrasound energy.

BACKGROUND

High intensity focused ultrasound (HIFU) has been used as a non-invasive precise treatment modality for internal pathological conditions such as tumors and abnormal vascular or nerve conditions. While diagnostic ultrasound has a focal intensity typically around 0.1 W/cm$^2$, high intensity focused ultrasound is of 4-5 orders of magnitude greater in focal intensity, typically in the range of 1,000 to 10,000 W/cm$^2$. HIFU energy, focused at locations deep in tissue, leaves the intervening tissue between the HIFU source and the focus unharmed. At the HIFU focus, however, the focal temperature may quickly exceed 70° C., and thereafter reach 100° C., the boiling point of tissue water, depending on the application of the HIFU energy. The high focal tissue temperature generated by the HIFU energy can rapidly cause tissue disruption. The thermal effect of tissue destruction is augmented further by the mechanical effect of HIFU energy. The combined thermal and mechanical effect at the tissue focus of the HIFU is being used for the treatment of uterine fibroid tumors, prostate hyperplasia or cancer, liver cancer, malignant bone and soft tissue sarcoma and internal bleeding.

Since HIFU treatment is mostly directed to internal pathological conditions, which cannot be visually seen, the use of radiologic imaging of those pathologies deep in the tissue is necessary for the therapy. MRI is being used to guide HIFU treatment of internal fibroids. Transabdominal ultrasound-guided HIFU treatment of liver tumors and uterine fibroids is also being practiced.

Recently, transvaginal ultrasound image-guided HIFU treatment of uterine fibroids has been developed. Similar technology can be applied to endometrial ablation and treatment of cervical neoplasia and HPV lesions. In order to properly treat the deep uterine pathologies, such as fibroids, it is preferred that the tumor along with the surrounding uterine tissue be visualized in real time throughout the HIFU treatment process. Both clear imaging by diagnostic ultrasound and achievement of HIFU tissue effect at the target area are important when conducting image-guided HIFU therapy.

In order to use ultrasound energy to image the structures of an area for treatment, the imaging scan head traditionally has to be in direct and firm contact with the tissue in continuum to the tissue of the target area. This engagement of the imaging scan head to the tissue may be supplemented by a coupling medium which can effectively transmit the ultrasound between the scan head and the tissue. For example, ultrasound gel is traditionally used to couple an ultrasound scan head and the skin on a person's abdomen to visualize intra-abdominal structures. The coupling material, such as ultrasound gel, is of similar acoustic transmission characteristics as that of the tissue to prevent an acoustic aberrance at the scan head-tissue interface. For example, if there is air or other obstructions between the scan head and the skin, the ultrasound imaging will become distorted or non-observable due to the difference of acoustic impedance of the air or other obstructions from that of the tissue. The ultrasound gel as a coupling medium replaces the air at the interface and enables clearer imaging of the underlying structures.

A conventional HIFU transducer generating therapeutic ultrasound energy likewise should be in direct engagement of the tissue in continuum with the target in order for the ultrasound energy to be effectively transmitted and focused at the target area to achieve the therapeutic effect. Generally, a coupling medium of similar acoustic characteristics as the tissue is used to connect the HIFU transducer with the tissue to enable optimal transmission and focusing of HIFU energy. Disengagement of the imaging scan head or the HIFU aperture from the tissue without a mechanism of coupling tends to interfere with the image-guided HIFU treatment of the target tissue.

For example, performing transvaginal ultrasound image-guided HIFU treatment of uterine fibroids requires a physical contact to obtain a proper engagement and coupling of an imaging probe and a HIFU transducer to the cervix and vaginal fornices. The imaging scan head needs to be placed firmly against the cervix and is generally pushed up towards the top of the anterior fornix to obtain optimal ultrasound images of the pelvic organs. Ultrasound gel is used to enhance the coupling between the scan head and tissue. Disengagement between the scan head and the cervix-fornices typically results in poor image quality. The HIFU transducer, which may be in a fixed relationship to the imaging head, engages the cervix, mostly towards the posterior fornix. Due to its size, the HIFU transducer also typically partially rides on the surface of the cervix that has the cervical os in its center. A fixed spatial relationship between the imaging head and the HIFU aperture presents an obvious challenge: optimal engagement of the imaging head with the tissue at the cervix may disengage the HIFU transducer from the cervical tissue toward the posterior fornix and vice versa. The variability of the dimensions and shape of the cervix and vaginal fornices among women makes it very difficult to design a probe that can optimize the simultaneous engagement of both the imaging and HIFU heads to the cervix and vaginal fornices. As noted earlier, when using conventional ultrasound systems, disengagement of the imaging head from the cervical tissue results in poor images of the pelvic organs. Disengagement of the HIFU transducer from the tissue toward the posterior fornix results in intervening air space that can cause aberration of the HIFU effect and even undesirable local heating at the tissue interface.

Thus, there is a need to provide consistent clear imaging of the target tissue and the HIFU effect at the target tissue to help guide movement of the HIFU focus throughout the procedure. Furthermore, there is a need for a more global approach for the engagement and coupling of both an imaging component and HIFU component to the tissue in a body cavity. These needs and other shortcomings in the prior art are addressed herein.

BRIEF SUMMARY

Methods and apparatus described are configured to use a fluid, such as water or normal saline, as a universal coupling medium between both an imaging scan head and the aperture of a HIFU transducer and the tissue of a patient to be treated. A body cavity of the patient is partially or fully filled with fluid and a combined imaging/high intensity focused ultrasound (HIFU) probe as described herein is immersed in the fluid. The fluid in the cavity allows the probe to deliver image-guided HIFU therapy in which direct engagement of the imaging scan head and/or the HIFU transducer to the tissue in the cavity is not necessary. The coupling effect of the fluid provides increased freedom for non-contact engagement of the imaging scan head and the HIFU transducer to the tissue to be treated. The method and the apparatus described herein are applicable to all body cavities, existing or created surgically.

An embodiment of a combined imaging/HIFU probe includes an imaging scan head for imaging target tissue in a patient and a HIFU transducer having an aperture through which HIFU energy is transmitted to the target tissue. A channel in fluid connection with an outlet port delivers a flow of fluid to the outlet port which directs the fluid across at least a portion of the aperture of the HIFU transducer. The probe is constructed to allow fluid flow from the outlet port to fill at least a portion of the body cavity in which the imaging scan head and HIFU transducer are immersed. The fluid provides a coupling for transmission of ultrasound energy between the probe and the patient.

In one aspect, the probe may be constructed to direct a flow of fluid toward an area of tissue in the body cavity near the aperture of the HIFU transducer. This flow of fluid flushes the area of tissue of obstructions to the transmission of HIFU energy to the target tissue.

In another aspect separate from or combined with the foregoing aspect, the probe may include a cuff that extends around the probe. The cuff is configured to obstruct an opening to the body cavity to help retain fluid from the outlet port in the body cavity.

In yet another aspect separate from or combined with either of the foregoing aspects, the probe may include a regulator configured to regulate fluid flow with respect to the body cavity according to a desired fluid pressure of the fluid in the body cavity.

In still another aspect separate from or combined with any of the foregoing aspects, the probe may include a cover in sealing engagement with the HIFU transducer, wherein the cover is comprised of a non-permeable material that has at least one perforation defined therethrough which allows fluid to flow through the cover.

Another embodiment of a combined imaging/high intensity focused ultrasound (HIFU) probe comprises an imaging scan head for imaging target tissue in the patient, a HIFU transducer having an aperture through which HIFU energy is transmitted to the target tissue, a channel in fluid connection with an outlet port for delivering a flow of fluid, and a cover in sealing engagement with the HIFU transducer. The cover is comprised of a non-permeable material that has at least one perforation defined therethrough that allows fluid to flow through the cover. Further, a flexible sheath overlies the cover and is sealingly engaged with the HIFU transducer. The probe is constructed to allow fluid flow from the outlet port to fill the space between the aperture of the HIFU transducer and the cover, and further to fill the space between the cover and the sheath, causing the sheath to inflate with fluid. The fluid flows through the at least one perforation in the cover and provides a coupling for transmission of ultrasound energy from the HIFU transducer to the patient.

Also disclosed herein are methods of deploying a combined imaging/HIFU probe for use in a body cavity of a patient. An embodiment of the method includes inserting the combined imaging/HIFU probe through an opening to the body cavity of the patient and directing a flow of fluid from the outlet port of the probe across at least a portion of the aperture of the HIFU transducer.

In one aspect, the method may further include directing fluid flow from the outlet port toward an area of tissue in the body cavity near the aperture of the HIFU transducer. The fluid flow is used to flush the area of tissue and reduce obstructions to the transmission of HIFU energy to the target tissue.

In another aspect separate from or combined with the foregoing aspect, the method may include positioning a cuff around the probe to obstruct the opening to the body cavity to help retain fluid from the outlet port in the body cavity.

In yet another aspect separate from or combined with either of the foregoing aspects, the method may include regulating fluid flow with respect to the body cavity according to a desired fluid pressure of the fluid in the body cavity.

In still another aspect separate from or combined with any of the foregoing aspects, the method may include covering the HIFU transducer with a cover comprised of a non-permeable material in sealing engagement with the transducer, wherein the cover has at least one perforation defined therethrough that allows fluid to flow through the cover.

Additional features of the above-identified apparatus and methods are described in the detailed description below, in combination with the drawings provided herewith.

DETAILED DESCRIPTION

A combined imaging/HIFU probe as described herein is deployed in a body cavity that is partially or fully filled with a fluid, such as but not limited to, water or normal saline. The fluid is used as a universal coupling medium between both an ultrasound imaging scan head and HIFU transducer of the combined probe and the tissue to be treated by the probe.

Figure 1:
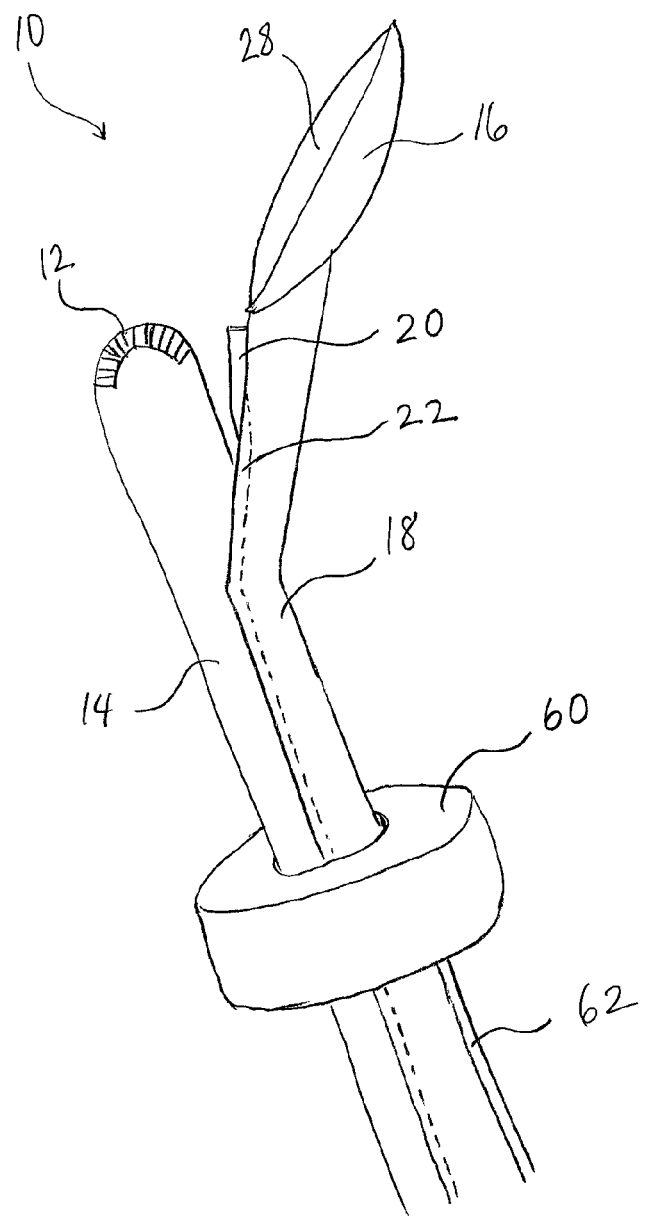
FIG. 1 illustrates an embodiment of a combined imaging/HIFU probe having an inflatable cuff extending around the shaft of the probe. Among other features, the probe includes a fluid outlet port at the proximal end of the HIFU transducer, though in other embodiments, the outlet port may be positioned at the distal end of the HIFU transducer or at other locations.

FIG. 1 illustrates an embodiment of a combined imaging/HIFU probe 10 for providing image-guided HIFU treatment of a pathology in a patient. As disclosed in at least one example for treatment of a uterine pathology (see, e.g., FIG. 2), a fluid, such as water, having acoustic transmission characteristics similar to that of tissue, can be used to fill the gap between the combined probe 10 (including both the imaging scan head 12 and the HIFU transducer 16) and the cervix and vaginal fornices of the patient to provide the necessary coupling. The fluid can fill any space of non-contact of the probe and tissue to provide optimal transmission of ultrasound energy for both imaging and therapy. Using fluid in this manner to provide a global coupling diminishes the need of perfect physical engagement between the ultrasound imaging and therapy heads to the cervix and vaginal fornices. This provides an important step towards improving the performance of transvaginal ultrasound image-guided HIFU treatment of pathologies, such as uterine fibroids and endometrial ablation.

With a fluid media, such as water or normal saline, filling the vaginal cavity (as shown, for example, in FIG. 2), the ultrasound imaging head does not need to be engaged firmly against the cervix or the fornices to obtain an optimal image of the pelvic structures. The fluid media in the vaginal cavity effectively communicates the ultrasound energy to the tissue to obtain images of the pelvis, even if the scan head is positioned away from the cervix or fornices, such as in the location of upper mid portion of the vaginal canal.

Furthermore, with a fluid filled vaginal cavity to facilitate engagement and coupling of the imaging scan head to the tissue structures in the vaginal cavity, different non-customized scan heads can be used, even off-the-shelf commercially available scan heads, including those for 3D/4D imaging. The method for global engagement described herein and the ultrasound coupling characteristics of a fluid-filled body cavity has broadened the form factor requirement of the imaging and therapy transducers in the application of ultrasound image-guided HIFU treatment of various pathologies.

The combined imaging/HIFU probe 10 depicted in FIG. 1 is configured for insertion into a body cavity of a patient. In this particular embodiment, the combined probe 10 includes an imaging scan head 12 for imaging target tissue in the patient. The imaging scan head 12 is shown located at or near a distal end of an imaging probe shaft 14. The proximal end of the imaging probe shaft 14 may extend outward from the body cavity of the patient to allow a physician to manipulate the position of the imaging scan head 12 within the body cavity.

The combined probe 10 further includes a HIFU transducer 16 having an aperture through with HIFU energy is transmitted to the target tissue in the patient. The HIFU transducer 16 is shown located at or near a distal end of a HIFU probe shaft 18 that is shown generally coupled to the imaging probe shaft 14. In this particular embodiment, the distal end of the HIFU probe shaft 18 projects away at an angle from the main axis of the imaging probe shaft 14. In this manner, the HIFU transducer 16 is spaced apart from the imaging scan head 12. Although not specifically depicted, the HIFU probe shaft 18 may include passages for electrical communication of signals from a signal source to the HIFU transducer 16 to enable the transducer 16 to produce appropriate pulses of HIFU energy for treatment of the patient. Similarly, the imaging probe shaft 14 may include passages for electrical communication between the imaging scan head 12 and external electronics that can receive imaging signals from the scan head 12 and produce images of the tissue being treated.

The combined imaging/HIFU probe 10 further includes an outlet port 20 that is configured to direct a flow of fluid across at least a portion of the aperture of the HIFU transducer 16. This flow of fluid helps prevent the transducer 16 and adjacent tissue of the patient from overheating when HIFU energy is being transmitted by the transducer 16. In FIG. 1, the outlet port 20 is positioned at a proximal end of the HIFU transducer 16. Within the HIFU probe shaft 18 is a channel 22 in fluid communication with the outlet port 20 for delivering a flow of fluid to the outlet port 20.

The probe 10 is further constructed to direct at least a portion of the fluid flow from the outlet port 20 toward an area of tissue in the body cavity near the aperture of the HIFU transducer 16. This fluid flow is configured to flush the area of tissue near the aperture of the HIFU transducer 16 to reduce obstructions to the transmission of HIFU energy to the target tissue. For example, fluid flowing from the outlet port 20 facilitates removal of bubbles, mucous, or other debris or material that may otherwise dissipate the HIFU energy being transmitted from the HIFU transducer 16 to the target tissue.

Further depicted in FIG. 1 is a water pillow 28 that extends across the aperture of the HIFU transducer 16. Although not necessary to the construction of the probe 10, the water pillow 28 can further assist in cooling the HIFU transducer 16 and adjacent tissue. If desired, fluids may be circulated in and out of the water pillow 28 via channels defined in the HIFU probe shaft 18 that are not shown in FIG. 1. Additionally, the water pillow 28 may assist with coupling the HIFU energy from the transducer 16 to the target tissue in the patient.

As will be appreciated from the disclosure herein, the probe 10 is constructed to allow fluid flowing from the outlet port 20 to fill at least a portion of the body cavity of the patient with fluid in which the imaging scan head 12 and the HIFU transducer 16 are immersed. The fluid in the body cavity, as previously noted, provides a global coupling for transmission of ultrasound energy between the combined imaging/HIFU probe and the patient.

Figure 2:
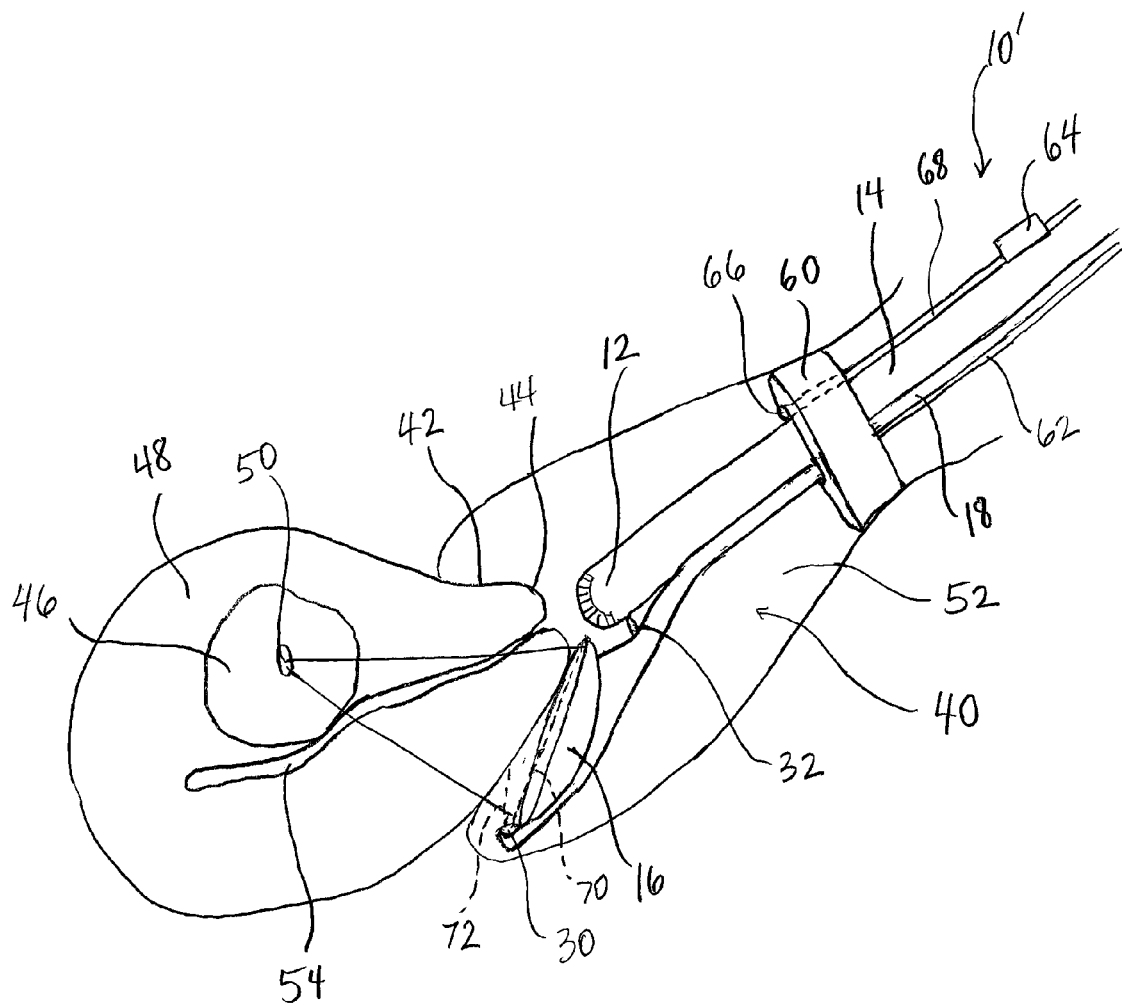
FIG. 2 illustrates the placement of a combined imaging/HIFU probe in the vaginal cavity of a female patient with the HIFU transducer positioned at the posterior fornix and the imaging scan head close to the cervix. As described herein, the cuff is inflated and the vaginal cavity is filled with fluid from the outlet port at the distal end of the HIFU transducer.

For example, water has acoustic characteristics that are similar to tissue and can communicate the HIFU energy in continuum from the HIFU transducer 16 to the HIFU focus 50 at the target tissue, as illustrated in FIG. 2. The HIFU transducer 16 thus need not be in direct contact with the tissue and additional coupling gels are not required. Using a fluid filled body cavity allows a variable placement of the HIFU transducer 16 in terms of angle of engagement and distance from tissue contact. This freedom of engagement broadens the targeting capacity of the HIFU transducer 16 since the HIFU transducer can be freely moved to change the location of the focus 50. Additionally, the non-contact engagement method as disclosed herein allows for manipulation of bodily structures, such as the cervix and uterus, to achieve a better and safer targeting path. This method also allows a variability in the shape and size of the HIFU transducer 16 since it is not necessary to match the anatomical contour of the cervix and vaginal fornices and achieve direct tissue contact for effective HIFU energy transmission. Furthermore, this method allows flexibility of the shape and tension of the cooling water pillow 28 (shown in FIG. 1) covering the HIFU transducer 16, again due to the absence of a requirement for direct contact of the water pillow 28 to the cervix and vaginal fornices.

As noted previously, fluid from the outlet port 20 may be used to flush the area of tissue in the body cavity near the HIFU transducer 16. The combined probe 10 may further be constructed to direct at least some of the fluid flow from the outlet port 20 to flush an area of tissue in the body cavity near the imaging scan head 12.

FIG. 2 illustrates an alternative embodiment of a combined imaging/HIFU probe 10' having multiple outlet ports. A first outlet port 30 is positioned at a distal end of the HIFU aperture 16 and is configured to direct fluid flow across at least a portion of the aperture of the HIFU transducer 16. The outlet port 30 also directs fluid toward an area of tissue in the body cavity near the aperture of the HIFU transducer 16 to flush the area of tissue of obstructions to the transmission of HIFU energy.

The combined imaging/HIFU probe 10' further comprises a second outlet port 32 that is positioned proximate to the imaging scan head 12 to direct a flow of fluid across at least a portion of the imaging scan head 12. Additionally, the probe 10' is constructed to direct at least a portion of the fluid flow from the second outlet port 32 to flush an area of tissue in the body cavity near the imaging scan head 12. The flushing action of the fluid from the second outlet port 32 helps reduce or remove any obstructions to the transmission of ultrasound energy between the imaging scan head 12 and the patient. By reducing obstructions near the imaging scan head 12, clearer images of the tissue being treated may be obtained.

With both embodiments of the probe 10 and 10' shown in FIGS. 1 and 2, or any of the other probe embodiments shown or discussed herein, the flow of fluid from the outlet ports 20, 30, 32 may be intermittent or continuous, as desired. A continuous flow of fluid from one or more of the outlet ports may be beneficial in maintaining cool temperatures of nearby tissue, especially tissue proximate to the HIFU transducer 16, as well as flushing obstructions that may develop at or near the HIFU transducer 16 or the imaging scan head 12.

In FIG. 1, the channel 22 that delivers fluid to the outlet port 20 (as well as channels (not shown) delivering fluid to the outlet ports 30, 32 in FIG. 2) may receive a flow of fluid from a receptacle that uses gravity to deliver the fluid to the channel 22. An IV bag filled with fluid, for example, may be elevated relative to the body cavity of the patient and deliver fluid under pressure of gravity to the outlet ports 20, 30, 32. In such embodiments, expensive fluid pumps are not necessary to provide pressure to the fluid being delivered to the outlet ports 20, 30, 32. Alternatively, an IV bag or other receptacle positioned lower relative to the body cavity may be used to provide a negative pressure to draw fluid out of the body cavity.

The combined imaging/HIFU probe 10' shown in FIG. 2 has been deployed in the vaginal cavity 40 of a female patient. More specifically, the probe 10' has been inserted through the vaginal canal of the patient with the HIFU transducer 16 placed at the posterior end of the vaginal fornix 42. The imaging scan head 12 is placed close to the cervix 44. For this particular example, the combined imaging/HIFU probe 10' is being used to treat a uterine fibroid 46 located in the myometrium 48 of the uterus. Depicted by lines illustrating a conical shape, HIFU energy transmitted by the transducer 16 is directed toward a focus 50 within the uterine fibroid 46. Through manipulation of either the probe 10' or the myometrium 48 containing the fibroid 46, the HIFU focus 50 is moved through the uterine fibroid 46 during treatment to destroy the fibroid tissue.

Fluid flowing from one or both of the outlet ports 30 and 32 is used to fill at least a portion of the vaginal cavity 40 with fluid 52. The imaging scan head 12 and the HIFU transducer 16 are immersed in this fluid 52. Depending on the pressure of the fluid 52 within the vaginal cavity 40, as well as the physiological state of the cervix 44, the fluid 52 may further flow into the endometrial cavity 54, thus filling the uterus with fluid as well. Filling the endometrial cavity 54 with fluid 52 may be desirable in that the fluid may assist with coupling HIFU energy transmitted from the HIFU transducer 16 to the focus 50 within the uterine fibroid 46.

Further illustrated with the embodiments of the combined probes 10 and 10' in FIGS. 1 and 2 is a cuff 60 that extends around the probe. The cuff 60 is configured to obstruct an opening to the body cavity to help retain fluid in the body cavity. For example, with respect to FIG. 2, the cuff 60 obstructs the opening of the vaginal canal and helps retain fluid 52 from the outlet ports 30 and/or 32 in the vaginal cavity 40. A passage for air to escape from the body cavity may be provided, especially during the time in which the body cavity is being filled with fluid. This passage may also be used to regulate the pressure of the fluid 52 in the body cavity by allowing a portion of the fluid in the body cavity to flow out past the cuff 60.

The cuff 60 can be of any size, shape, or construction. Preferably, the cuff 60 is tailored to the anatomy of the patient to retain fluid in the particular body cavity. In use, the cuff 60 may be positioned at any location along the shaft of the probe as needed to address the particular shape and position of the opening to the body cavity to retain the fluid in the body cavity. An outer surface of the cuff 60 preferably provides a sealing engagement with the opening to the body cavity and an inner surface of the cuff 60 preferably seals against the shaft of the probe. The inner surface of the cuff 60 may be constructed with a flexible material that permits the probe to pivot and/or translate within the cuff while maintaining a seal against the shaft of the probe. For example, with respect to the probe 10' shown in FIG. 2, the shaft of the probe 10' may translate within (i.e., slide in and out of) the vaginal cavity 40 along the main axis of the probe through the interior surface of the cuff 60. The probe 10' may also rotate circumferentially within the interior surface of the cuff 60 and also pivot in multiple directions at the level of the cuff to allow proper positioning of the HIFU aperture 16 and the imaging scan head 12 within the patient. The freedom of movement of the probe 10' through the cuff 60 may be achieved by using a pliable material, such as latex, polyurethane, or other suitable material, to form a ring around the shaft of the probe 10'. The flexibility of this pliable material allows for movement of the probe, yet is able to prevent fluid leakage along the shaft of the probe.

The cuff 60 may be constructed to expand to a desired size that matches the anatomical features of the body cavity opening. While various forms of the cuff 60 can be constructed using mechanical elements to expand the cuff, the cuff 60 depicted in FIGS. 1 and 2 is constructed to be inflatable. A fluid line 62 to the cuff 60 may be incorporated in or along the HIFU probe shaft 18 or the imaging probe shaft 14 to inflate the cuff 60 using a gas or liquid fluid medium. The amount of inflation of the cuff 60 can be varied to suit the need for occlusion of the orifice to retain fluid in the body cavity. Moreover, the inflation can be adapted to allow the sliding of the probe through the cuff as well as rotation and pivoting of the probe within the cuff to allow the position of the probe to be manipulated within the body cavity for imaging and HIFU treatment.

The combined imaging/HIFU probe 10' shown in FIG. 2 further includes an inlet port 66 in fluid connection with a channel 68 that is configured to convey fluid 52 out of the body cavity 40. The inlet port 66 and channel 68 are shown connected to the probe shaft 14 and passing through the interior of the cuff 60. In other embodiments of the probe, an inlet port such as the inlet port 66 may be placed anywhere with respect to the probe and/or the cuff, provided the inlet port 66 has access to the fluid 52 in the body cavity.

It will be appreciated that, when using a cuff 60 or otherwise causing fluid to be retained in the body cavity, the fluid filling the body cavity has a fluid pressure that bears against the sides of the body cavity as well as the tissue structures within the body cavity. In such cases, the pressure of the fluid in the body cavity may be capable of distending the tissue in the body cavity. For example in FIG. 2, considering the situation in which fluid 52 passes through the cervix 44 into the endometrial cavity 54, the pressure of the fluid in the endometrial cavity 54 may cause the cavity 54 to expand against the myometrium 48, thus moving the myometrium (including the fibroid 46) from one position to another. As depicted, the HIFU transducer 16 transmits HIFU energy to a focus 50 within the fibroid 46. By increasing or decreasing the fluid pressure within the endometrial cavity 54, the position of the target tissue in the fibroid 46 may be modified relative to the focus 50 of the HIFU energy. Accordingly, it is possible to position the target tissue in the fibroid 46 relative to the focus 50 by modifying the fluid pressure in the endometrial cavity 54 without moving the position of the HIFU transducer 16.

To achieve a desired fluid pressure in the body cavity (whether it be the vaginal cavity 40, the endometrial cavity 54, or other body cavity), a combined imaging/HIFU probe such as the probe 10' may be provided with a regulator 64 that is configured to regulate the fluid flow with respect to the body cavity. In an embodiment of the probe 10' as shown in FIG. 2, the regulator 64 may be coupled to the channel 68 through which fluid 52 flows out of the body cavity 40. The regulator 64, which may be a valve, for example, is adjusted to regulate the amount of fluid 52 flowing out of the body cavity. If a greater amount of fluid is flowing into the body cavity through the outlet ports 30, 32 than is flowing out of the body cavity through the inlet port 66, the pressure of the fluid 52 in the body cavity will tend to increase. The pressure of the fluid 52 in the body cavity may decrease if a greater amount of fluid is allowed to flow out of the body cavity than is flowing into the body cavity. Accordingly, a desired pressure of the fluid in the body cavity may be obtained. By monitoring the images obtained by the image scan head 52, a physician operating the probe 10' may observe the movement of tissue relative to a focus 50 of the HIFU energy being transmitted by the probe, and regulate the fluid pressure in the body cavity to cause tissue structures such as the fibroid 46 to move relative to the focus 50 without moving the position of the HIFU transducer 16.

In this manner, the imaging scan head 12 and HIFU transducer can be held stationary, such as against the posterior vaginal wall, and at the same time the cervix and uterus can be moved relative to the HIFU transducer 16 by changing the vaginal volume as distended by the infused fluid 52. As the vaginal fluid volume increases, the cervix and uterus gradually move away from the stationary HIFU transducer. Deflating the fluid volume of the vaginal cavity 40 will do the opposite. This relative movement of the uterus with respect to the HIFU transducer 16 will allow the HIFU focus 50 to move within the uterine tissue without moving the transducer 16. The rate of movement can be finely controlled by the fluid inflow or outflow at varying rates. If needed, the HIFU transducer 16 can be systematically moved back against the fixed vaginal wall to different positions to control the other two axis of the HIFU focus. The ability to brace the combined imaging/HIFU probe against the fixed vaginal wall can allow the clinician more control in handling the probe in a steady way. Alternatively, a mechanical arm can be used to hold the probe steady in a location in the vagina and then use the fluid volume to move the HIFU focus 50 as described above.

In at least one alternative embodiment, a separate structure such as a valve may not be necessary in order to implement the regulator 64. For example, the fluid flowing out of the body cavity through the channel 68 may be regulated by using the inflatable cuff 60 to selectively compress the size of the channel 68 within the cuff 60. By allowing the inflation of the cuff 60, or some portion thereof, to selectively constrict the channel 68, a variable amount of fluid flowing out of the body cavity may be obtained to adjust the pressure of the fluid remaining within the body cavity. In yet other alternative embodiments, the regulator 64 may be constricted to adjust the amount of fluid flowing into the body cavity through the outlet port(s). For example, referring to FIG. 1, the regulator 64 may be coupled to the channel 22 to selectively adjust the amount of fluid flowing to the outlet port 20. Also, as previously discussed, the cuff 60 may be constructed such that selective adjustment of the inflation of the cuff 60 using the cuff inlet 62 may be used to selectively constrict the channel 22 and, thus, selectively adjust the amount of fluid being delivered to the outlet port 20 according to a desired fluid pressure in the body cavity. In such alternative embodiments, the regulator 64 may be considered incorporated into the cuff 60.

By adjusting the fluid flow with respect to the body cavity throughout a transmission of HIFU energy to the focus 50, the range of target tissue to be treated by the HIFU energy may be directed through the focus 50 without moving the position of the HIFU transducer 16. Where the regulator 64 is incorporated into the cuff 60, the cuff 60 is configured to adjust the fluid flow out of the body cavity throughout the transmission of HIFU energy and thereby direct the range of target tissue to be treated by the HIFU energy.

Outlet ports, such as the outlet ports 20, 30, 32 of the combined imaging/HIFU probes described herein, may assume various forms and configurations as desired. For example, in one embodiment as depicted in FIG. 2, the outlet port 30 may be comprised of a nozzle that directs a flow of fluid 70 from the outlet port 30 across at least a portion of the aperture of the HIFU transducer 16. Additionally, the nozzle may direct a flow of fluid 72 in a single fluid path toward an area of tissue near the aperture of the HIFU transducer 16 to flush the area of tissue of obstructions, as previously described herein.

Figure 3A:
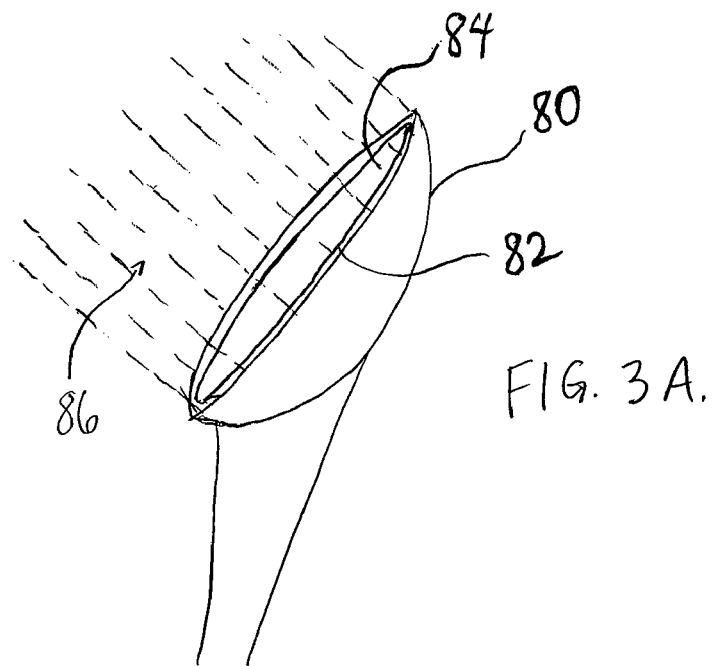
FIGS. 3A and 3B illustrate alternative configurations of a HIFU transducer with a fluid outlet part having nozzle(s) placed at various locations relative to the aperture of the HIFU transducer.

FIG. 3A illustrates another embodiment of a HIFU transducer 80 that may be used with the combined imaging/HIFU probe described herein. The HIFU transducer 80 has an outlet port 82 from which fluid may flow. In this particular embodiment, the outlet port 82 extends around the aperture 84 of the HIFU transducer 80 and directs the fluid flow 86 in a cylindrical- or conical-shaped fluid path. When the HIFU transducer 80 is next to an area of tissue, the fluid flow 86 may act to flush the area of tissue as well as flow across at least a portion of the aperture 84 to keep the tissue and the HIFU aperture at an acceptable temperature. In FIG. 3A, the fluid flow 86 is depicted by a series of dotted lines. However, it should be readily understood that the fluid flow 86 may be considered flowing in a single fluid path as fluid flows uniformly outward from the outlet port 82 around the circumference of the aperture 84.

Figure 3B:
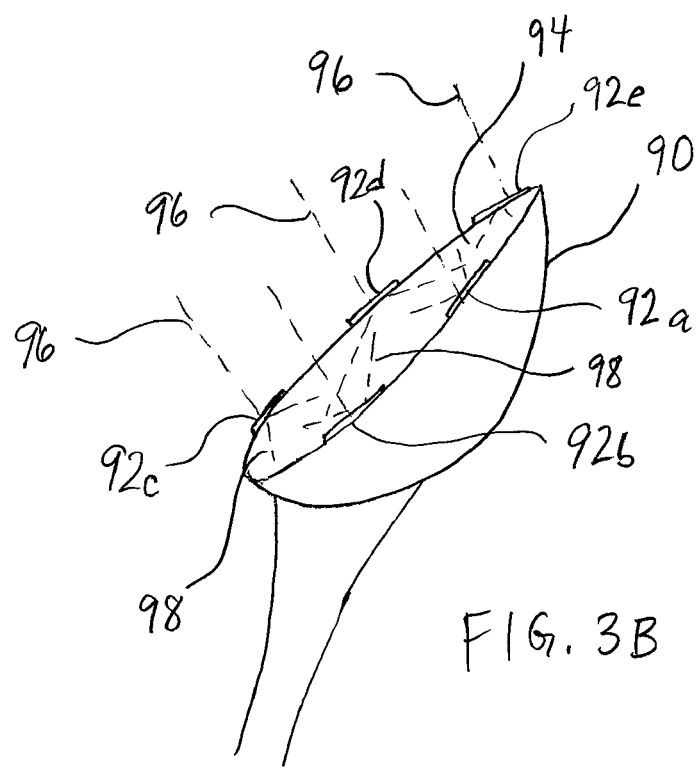

FIG. 3B illustrates another alternative embodiment of a HIFU transducer 90 that may be used with the combined imaging/HIFU probe described herein. In this embodiment, the HIFU transducer 90 has an outlet port comprised of multiple nozzles 92*a-e* that are spaced around aperture 94 of the HIFU transducer 90. The nozzles 92*a-e* are configured to direct fluid flow in multiple fluid paths 96 toward an area of tissue near the HIFU transducer 90 to be flushed. Furthermore, the nozzles 92*a-e* may be configured to direct a flow of fluid 98 across at least a portion of the aperture 94 of the HIFU transducer 90. For illustrative purposes, the multiple nozzles 92*a-e* are shown positioned in a ring around the aperture 94. While the nozzles are shown evenly spaced, in other embodiments the nozzles may be positioned with uneven spacing with respect to the aperture 94.

Figure 6:
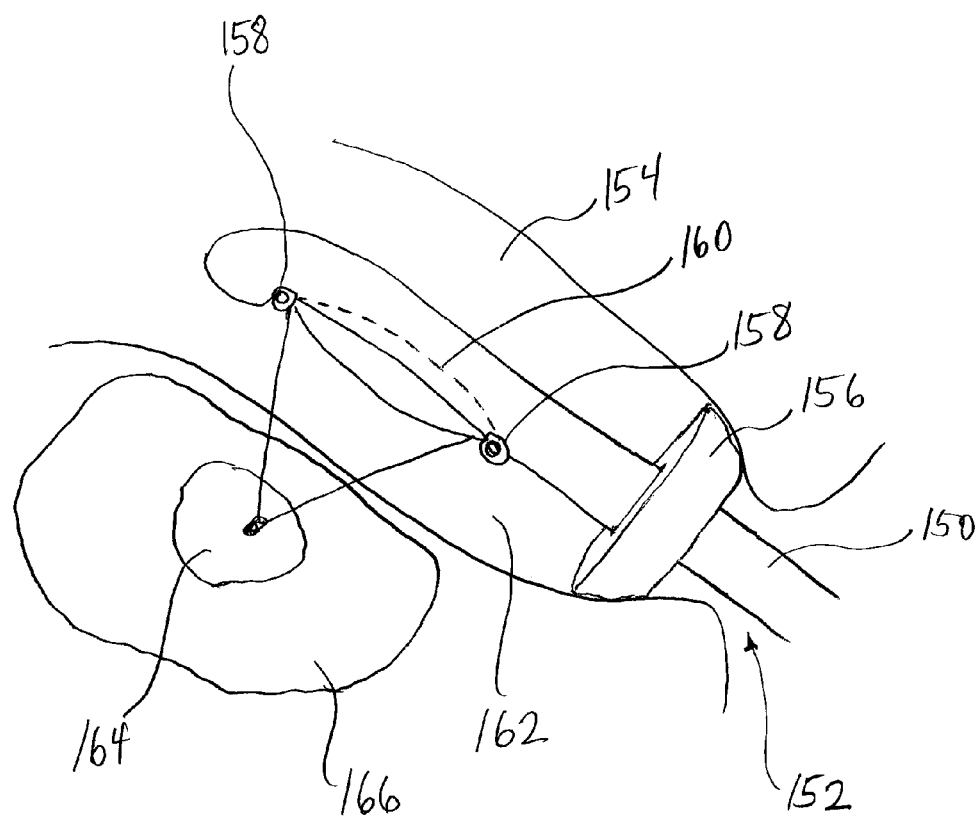
FIG. 6 illustrates a transrectal HIFU treatment of a prostate tumor. A cuff is deployed inside the rectum, which is filled with fluid. In this example, the combined imaging/HIFU probe has fluid outlet ports at both the proximal and distal ends of the HIFU transducer.

It should be readily appreciated that the filling a body cavity with fluid for global engagement and coupling of an imaging scan head 12 and HIFU transducer 16 to tissue for image-guided HIFU therapy can be applied to any cavity or space, existing or created, in a body. One example described above and shown in FIG. 2 is the vaginal cavity wherein HIFU energy is transmitted for treatment of a uterine fibroid. Another example is the rectal cavity for treatment of pathologies in the prostate gland (e.g., as shown in FIG. 6), the uterus and adnexal structures. Another example is the colon for treatment of colonic polyps or neoplasia. Yet another example is to fill the esophagus partially or fully with fluid to treat target tissue in the mediastinum such as tumors or nerves, or even target tissue in the heart for ablation purposes. Still another example is to flood the stomach with a fluid to treat stomach neoplasm using HIFU.

Figure 5:
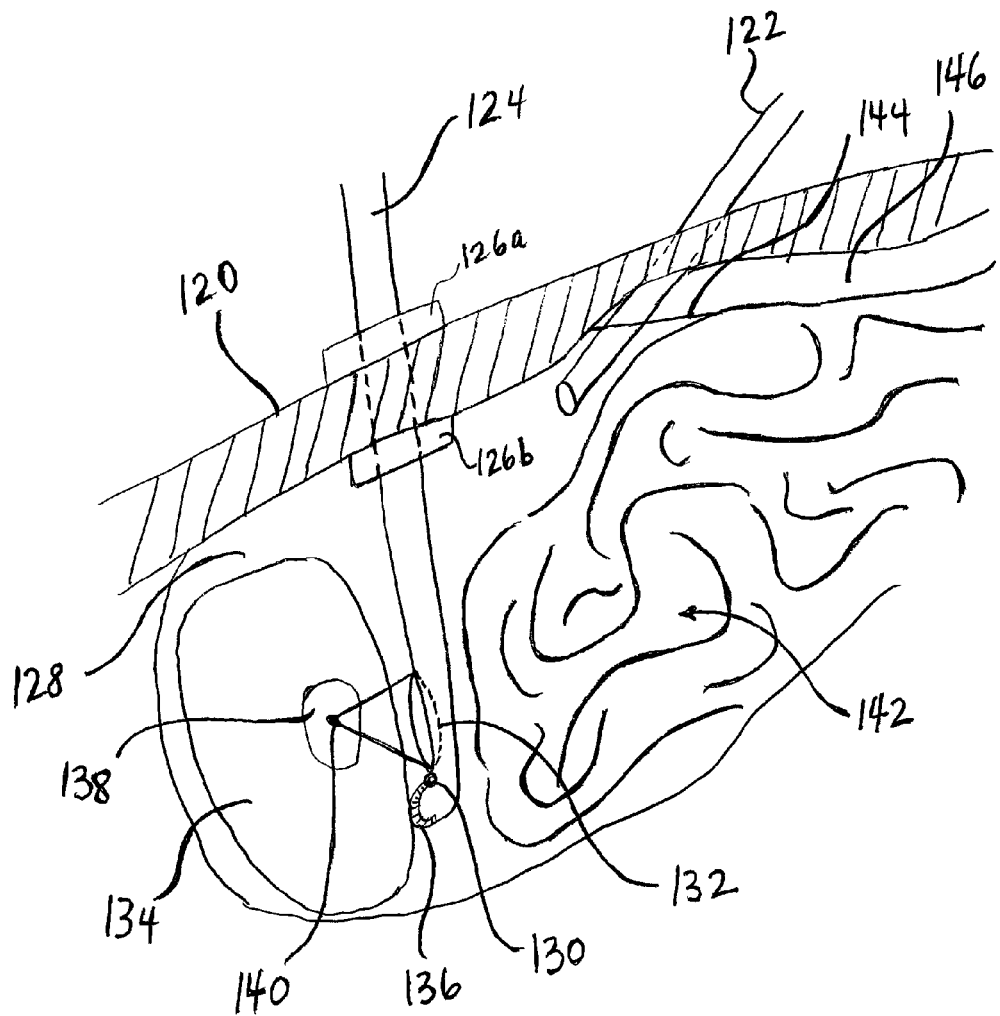
FIG. 5 illustrates an intra-abdominal application of image-guided HIFU therapy of a liver tumor. In this example, a double set of cuffs are deployed. The abdominal cavity is partially filled with a liquid and the remainder with a gas. A laparoscope may be used to visually assist the placement of the combined imaging/HIFU probe.

Yet another example is to fill the abdominal cavity to treat the liver (e.g., as shown in FIG. 5), pancreas, kidney, bowel, uterus, adnexal organs and other intra-abdominal organ targets. Pathologies to be treated can be tumors, blood vessels, and nerves and other pathologies.

In all, combined imaging/HIFU probes can be inserted into cavities and spaces including those cavities and spaces mentioned above and flooded with a fluid to perform image-guided HIFU therapy as described herein. Again, a benefit of this global engagement and coupling method allows a flexible form factor design for both the imaging and HIFU heads.

Figure 4:
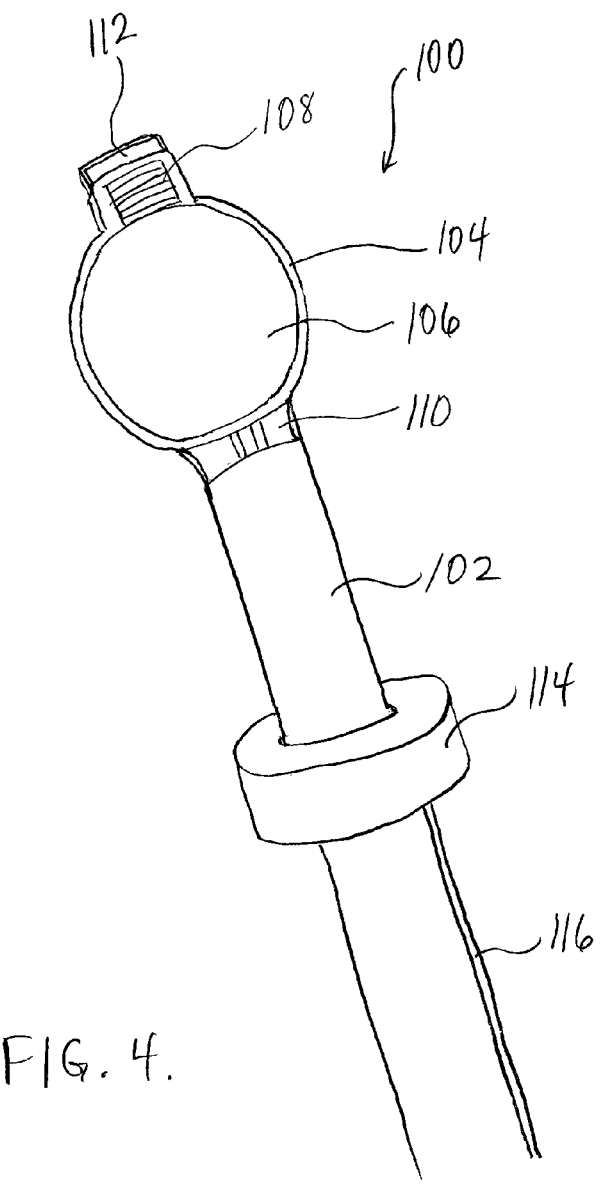
FIG. 4 illustrates a combined imaging/HIFU probe that can be used, for example, with intra-abdominal or transluminal applications. In this example, an inflatable cuff provides fluid blockage and a fluid outlet port is positioned at the distal end of the probe.

FIG. 4 depicts a probe 100 having a combined head for imaging and HIFU therapy. The probe 100 includes a shaft 102 to which a HIFU transducer 104 is connected. The HIFU transducer 104 includes an aperture 106 from which HIFU energy is transmitted to target tissue in the patient. Combined with the HIFU transducer 104 is an imaging scan head 108 shown positioned at a distal end of the HIFU transducer 104. The imaging scan head 108 is used to image the tissue being treated. The combined imaging scan head 108 and HIFU transducer 104 is connected to the probe shaft 102 via a hinge 110. The hinge 110 provides a point of articulation around which the combined head can be rotated to optimize the imaging and therapy delivery.

Further depicted in FIG. 4 is a cuff 114 that extends around the shaft 102 of the probe 100. As with other embodiments of the combined imaging/HIFU probe previously described, the cuff 114 may be inflated to a desired size using a fluid flowing through an inlet 116 to the cuff 114. The cuff 114 is used to occlude an opening to the body cavity into which the probe is inserted and to retain fluid in the body cavity at a desired pressure.

An advantage of using a probe with a combined imaging scan head and HIFU transducer as shown in FIG. 4 is that such a probe can be inserted into areas of the body that may otherwise be poorly visualized by other means. For example, as will be discussed in greater detail below, a physician can manipulate a combined probe 100 through a small abdominal incision into a fluid filled upper abdomen (with patient in the Trendelenburg position, for example) to place the probe 100 against the surface of an organ, such as the liver, e.g., as illustrated in FIG. 5. The physician can then use ultrasound images obtained from the imaging scan head to guide the transmission of HIFU energy from the probe to treat tumors, blood vessels, bile ducts or other targets. Using a combined imaging/HIFU probe in this manner helps alleviate the concern of inadequate visual imaging through a laparoscope, for example, due to anatomical position or obstructed background (such as by blood) in the fluid.

The following examples are provided to illustrate some applications in which the method and apparatus of the present invention may be used. These examples are by no means exclusive and the combined imaging/HIFU probes described herein are certainly not limited to use in the applications stated in these examples. There are many possible applications in which a combined imaging/HIFU probe may be inserted into a naturally existing or surgically created body cavity and filled partially or fully with fluid, particularly for treatment of intra-tissue pathologies that are otherwise not visible.

Example 1

As depicted in FIG. 2, the first example involves inserting a combined imaging/HIFU probe 10' into the vaginal cavity 40 of a patient in the Trendelenburg position and filling the vaginal cavity with fluid 52. In this example, the probe 10' includes one or more fluid outlet ports. A first outlet port 30 is located at a distal end of the HIFU transducer 16, while a second outlet port 32 is located adjacent to the imaging scan head 122. An inflatable cuff 60 that extends around the shaft of the combined probe 10' is expanded just internal to the vaginal introitus to retain the fluid 52 within the vaginal cavity 40. The cuff 60 can, but need not be, tightly fitted to the walls of the vaginal canal. In cases where fluid 52 is allowed to seep out past the cuff, for example through the channel 68, the fluid flow rate into or out of the vaginal cavity 40 can be used to control the degree of distention of tissue in the vaginal cavity. Alternatively, in cases where the cuff is tightly fitted to the vaginal canal, the fluid 52 can be retained in the vaginal cavity 40 without any spillage. The combined probe 10' can translate in and out through the cuff 60 and pivot freely in order to manipulate the placement of the probe. If desired, one or more seals may be fitted to the cuff 60 around the shaft of the probe 10', preferably toward the inside of the vaginal cavity 40, to bear against the pressure of the fluid 52 in the cavity and to help prevent unwanted seepage of fluid around the probe. The vaginal cavity 40 can be distended by allowing fluid to flow into the cavity by gravity or by a fluid pump. To decrease the distention of the vaginal cavity by fluid, the fluid 52 can be drained out through a separate channel 68 or by using the same tubing by reversing the gravity effect or the pump direction, or by allowing fluid to simply seep past the cuff 60.

With fluid filling the vaginal cavity, the imaging scan head 12 can either be in contact with or away from the tissue of the cervix 44 or vaginal fornices 42 and continue to image the pelvic organs using the fluid 52 as an acoustic conduction medium. The fluid 52 in the vaginal cavity 40 also enables HIFU energy to be transmitted from the HIFU transducer 16 through the fluid and focused at the target tissue in the uterus without the need of direct contact of the HIFU transducer 16 to the cervical/vaginal fornix tissue. The HIFU transducer 16 can be moved in multiple directions within the fluid filled cavity 40 to move the focus 50 within the uterine tissue. Alternatively, the HIFU transducer 16 may be held stationary, such as against the vaginal wall. Then by expanding or contracting the vaginal cavity with pressure from the fluid 52, the effect of the HIFU energy at the stationary focus 50 within the target tissue can be moved by moving the tissue away from or towards the HIFU focus 50. This method provides an effective use of image-guided HIFU therapy to treat a uterine pathology, such as fibroids.

Example 2

A small incision is made through the anterior abdominal wall 120, as shown in FIG. 5, with the option of doing so under visualization of a laparoscope 122. A combined imaging/HIFU probe 124 is then inserted directly through the abdominal incision, possibly through a cuffed conduit. The cuffs 126a and 126b which extend around the probe shaft are inflated to seal off the incision. Depending on the configuration of the cuffs 126a, 126b, the shaft of the probe 124 can slide in and out and pivot through the cuffs. Fluid 128 is fed into the abdominal cavity through tubing within or along the side of the probe 124 to an outlet port 130 near the HIFU transducer 132. The abdominal cavity is filled with the fluid 128, such as normal saline, aided by the patient being in the Trendelenburg position. The combined probe 124 is then guided towards the liver 134, in this example, by feel or by laparoscopic visualization, and then eventually by ultrasound imaging using the imaging scan head 136 of the probe 124. Once the imaging scan head 136 and HIFU transducer 132 are near to the surface of the liver 134, image-guided HIFU treatment of an intra-hepatic lesion 138, for example, can be performed. The focus 140 of the HIFU energy is moved throughout the liver tumor 138 to cause necrosis of the target tissue, either by moving the HIFU transducer 132 or by moving the tumor 138 by distending surrounding tissue according to pressure of the fluid 128 in the abdominal cavity. Ideally, when positioning the probe 124, the physician ensures the absence of any bowel loop 142 or other obstructions or air bubbles at the interface between the imaging scan head 136, the HIFU transducer 132, and the liver 134. Flushing of the tissue at the interface may be accomplished using fluid from the outlet port 130 in a manner as previously described.

It should be understood that, in this example or other examples or embodiments described herein, a gas fluid may also be introduced into the body cavity, particularly to influence the pressure of the liquid fluid in the body cavity to distend the tissues in the body cavity. For example, as illustrated in FIG. 5, the abdominal cavity is partially filled with a liquid fluid 128 up to a fluid level 144. The remaining portion of the abdominal cavity is filled with a gas 146, such as carbon dioxide. The fluid pressure in the abdominal cavity can thus be adjusted by regulating the amount of gas 146 or liquid fluid 128 in the abdominal cavity.

Example 3

A combined imaging/HIFU probe 150 is inserted through the anus 152 into the rectum 154, as illustrated in FIG. 6. A cuff 156 around the probe 150 may be inflated to fit against the rectal wall. The probe 150 can slide in and out and pivot freely through the cuff 156. The rectum 154 is filled with fluid flowing from the outlet ports 158 around the HIFU transducer 160. The patient may be in the reverse Trendelenburg position to facilitate the fluid 162 filling the rectum 154. Using the fluid 162 as a global engagement and coupling medium, image-guided HIFU treatment of a prostate tumor 164 in the prostate gland 166, for example, can be performed. Using the methods and apparatus of this disclosure, the prostate gland 166 and the pathology 164 within can be visualized using the imaging scan head 168 and treated with HIFU energy with a greater degree of accessibility.

Even in the presence of visual guidance, a distinct advantage of an image-guided HIFU treatment system as described herein is that the ultrasound imaging can see beyond the surface of the target organ. For example, ultrasound imaging can see a tumor deep within liver tissue as illustrated in FIG. 5. It can also see bleeding blood vessels deep in the liver, especially with a Doppler mode, while neither of these pathologies can be seen by laparoscopy. Similar examples can be applied to cases of intramural fibroids in the uterus, deep pancreatic tumors, etc., all of which are not visible by laparoscopy but can be imaged by ultrasound, especially using the global engagement and coupling methods described herein.

As illustrated in FIGS. 1 and 2, a fluid input line to the cuff 60 can be incorporated in or along the sides of the shaft of the combined imaging/HIFU probe. One or more fluid outlets 20, 30, 32 can be provided at the distal end proximal end, or at different positions around the HIFU transducer 16 and/or imaging scan head 12, or elsewhere on the probe. Preferably, the flow of fluid from the outlets 20, 30, 32 can be directed in various directions to flush any gas bubbles or debris away from the interface between the HIFU transducer 16 and the tissue nearby. Alternatively, a fluid line with an outlet port can be placed apart from the combined probe at a portion of the cavity, preferably the most dependent part of the cavity, to fill the cavity with the fluid. Another alternative is to have a fluid outlet port attached to the tip of an optical scope, such as laparoscope, or at the end of a hysteroscope or cystoscope, to be deployed in the body cavity in concert with the combined imaging/HIFU probe to visually direct the fluid flow to fill the cavity and to wash away gas bubbles and debris and double check the location of the combined probe and clearance of the HIFU path.

The fluid 52 can be water or more ideally an isotonic aqueous solution such as normal saline to avoid hypotonic fluid absorption into the body. The fluid 52 can be degassed as needed. The intake of the fluid 52 into the transport tubing (e.g., channel 22) can be as simple as an IV bag with gravity flow or a fluid infusion pump.

Figure 7A:
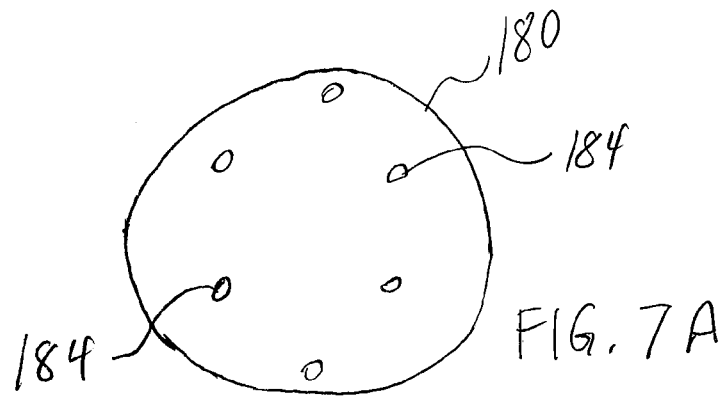
FIG. 7A illustrates a front view of a cover comprised of a non-permeable material that may be used to cover the aperture of a HIFU transducer. The cover includes one or more perforations that allow fluid to flow through the cover.
Figure 7B:
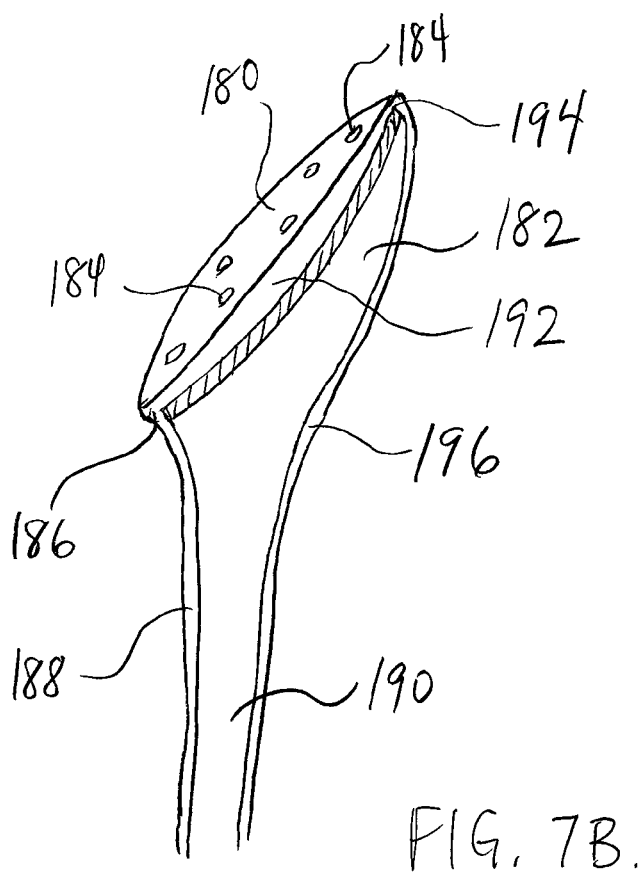
FIG. 7B illustrates a side section view of a HIFU transducer with a cover as illustrated in FIG. 7A. The HIFU transducer may be used in one or more of the combined imaging/HIFU probes described herein.

In yet another aspect, a combined imaging/HIFU probe as described herein may include a cover 180 extends over the aperture of the HIFU transducer 182, as illustrated in FIGS. 7A and 7B. The cover 180 is comprised of a non-permeable material and can be rigid, semi-rigid, or pliable, as desired. In at least one embodiment, the cover 180 is sealingly engaged with the HIFU transducer 182 and has at least one perforation 184 defined therethrough to allow fluid to flow through the cover.

In FIG. 7B, the HIFU transducer 182 includes an outlet port 186 shown positioned between the cover 180 and the aperture of the HIFU transducer 182. A first channel 188 in the shaft 190 of the probe delivers fluid to the outlet port 186, which flows out into the space 192 between the HIFU transducer 182 and the cover 180. The fluid circulates within the space 192 under the cover 180. The fluid may then exit through the one or more perforations 184 in the cover to fill the body cavity. In this manner, the fluids circulating in the space between the cover 180 and the HIFU transducer 184 serves to cool surface of the HIFU transducer and to provide an ultrasound coupling media between the HIFU transducer 182 and adjacent tissue. If desired, the fluid can be chilled to enhance the cooling effect.

The fluid from the outlet port 186 may further be configured to flow through the one or more perforations 184 in the cover toward an area of tissue in the body cavity near the aperture of the HIFU transducer 182. The fluid thus expelled through the one or more perforations 184 can serve to flush away any gas bubbles, mucus, or other debris at the interface between the aperture of the HIFU transducer 182 and the adjacent tissue.

As stated elsewhere herein, the fluids supplied to the HIFU transducer 182 can be pressurized by a gravity-fed IV bag system or by a fluid pump. The infusion rate and pressure of the fluid in the body cavity can be adjusted to meet various perfusion and tissue positioning requirements.

In the embodiment shown in FIG. 7B, the HIFU transducer 182 further includes an inlet port 194 positioned between the cover 180 and the HIFU transducer 182. The inlet port 194 is connected to a second channel 196 that conveys fluid away from the HIFU transducer 182. In this embodiment, fluid in the space 192 that does not otherwise flow out of the perforations 184 into the body cavity may flow into the inlet port 194 and away from the body cavity. The flow of the fluid from the HIFU transducer 182 through the inlet port 194 may be higher than the flow of fluid from the HIFU transducer 182 through the at least one perforation 184 in the cover 180. Accordingly, the probe may provide greater circulation of fluid into and within the space 192 than otherwise flows out through the one or more perforations 184 into the body cavity.

Since the fluid in the body cavity can effectively communicate both the imaging ultrasound and the therapeutic HIFU energy from the probe without requiring direct contact with the cervical or vaginal fornix tissue, there is a greater ability to vary the physical form factors of the imaging scan head 12 and the HIFU transducer 16. These form factors can be designed to facilitate the insertion of the combined probe through various body cavity openings, such as the vaginal introitus. The imaging scan head 12 and the HIFU transducer 16 can be inserted simultaneously or in sequence. The form factors can be tailored to the anatomy of different patients and optimized for deployment of the probe within a particular body cavity. The freedom to vary the form factors of the combined probe allows the use of different imaging and therapeutic heads, including from off-the-shelf commercial sources.

Figure 8:
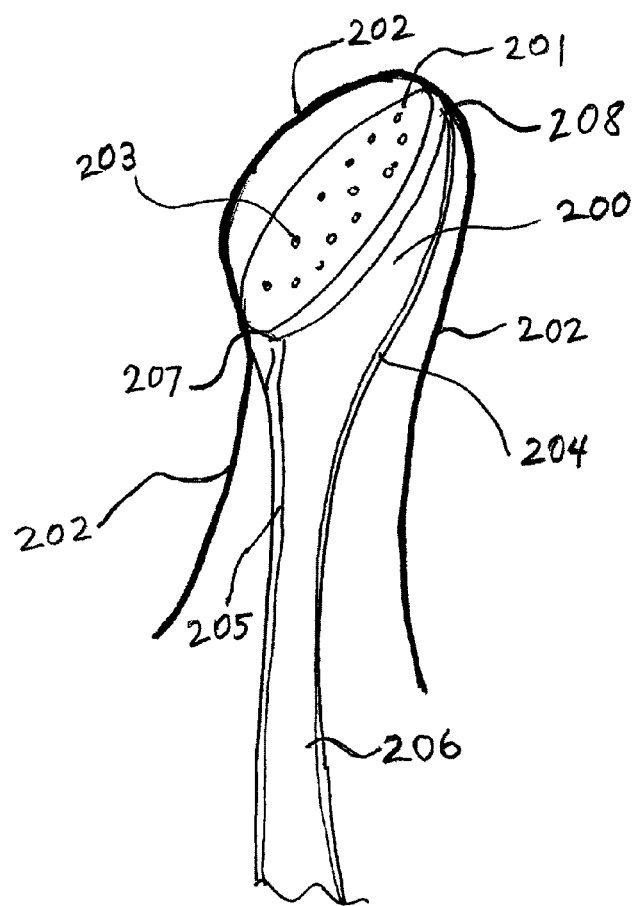
FIG. 8 illustrates a side section view of the HIFU transducer and cover as illustrated in FIG. 7B, and further encompassed by a fluid-filled sheath.

FIG. 8 illustrates a side section view of the HIFU transducer and cover as illustrated in FIG. 7B. The HIFU transducer 200 is covered with a cover 201 comprising a rigid, semi-rigid, or pliant membrane. A flexible sheath 202 overlies the cover 201 and preferably is sealingly engaged to the circumference of the HIFU transducer 200. Fluid flowing through a first channel 205 to an outlet port 207 fills the space between the aperture of the transducer 200 and the cover 201. The fluid also fills the space between the cover 201 and the sheath 202, causing the sheath 202 to inflate with fluid. One or more perforations 203 in the cover 201 allows fluid to flow from the space between the transducer 200 and the cover 201 into the space between the cover 201 and the sheath 202, or vice versa. Some or all of the fluid in the space between the transducer 200 and the cover 201 or the space between the cover 201 and the sheath 202 flows away from the transducer 200 through inlet port 208 via a second channel 204, especially once the fluid pressure under the sheath 202 reaches an equilibrium with the fluid pressure in the space between the transducer 200 and the cover 201.

With the probe configuration shown in FIG. 8, an acoustic coupling between the HIFU transducer 200 and adjacent tissue in the patient is obtained by inflating the flexible sheath 202 with fluid and then pressing the sheath 202 against the tissue. When inflated with fluid, the flexible sheath 202 is able to conform more closely to irregular features of the tissue and thus improve the coupling of HIFU energy from the transducer 200 to the tissue. As to the remainder of the sheath 202, after connecting to the periphery of the cover 201, the sheath 202 may extend along the shaft 206 of the transducer 200 to cover the shaft and help prevent communication of contamination in the body cavity.

The cover 201 can help prevent tissue or other objects from applying direct pressure to face of the transducer 200, thereby reducing the risk of transducer damage or tissue burns. Moreover, the same cooling fluid can be circulated over the surface of the transducer 200 and within the flexible sheath 202 to cool both the HIFU transducer 200 and the tissue adjacent to the sheath. A sufficient convective heat exchange can be obtained, even at a steady-state inflation of the sheath 202, to help maintain temperature equilibrium between the fluid within the cover 201 and any fluid outside the cover 201.

In some circumstances, it may not be practical or desirable to fill a surrounding cavity (assuming there is a cavity) with uncontained fluid. For example, a physician may want to effectively couple HIFU energy transmitted from the transducer 200 to adjacent tissue in the patient, particularly where there the transducer 200 is used outside a cavity in the body or is used within a body cavity, but the physician or patient wants to avoid fluid coming in direct contact with the walls of the cavity. In any case, benefits of the global fluid coupling described herein may be obtained with a fluid-filled sheath configuration as illustrated in FIG. 8. It is not necessary that the HIFU transducer 200 be directly pressed against tissue of the patient. Rather, the fluid-filled sheath 202 is pressed against the tissue and provides a coupling for transmission of HIFU energy from the transducer 200 to the tissue to be treated. In some embodiments, the sheath 202 further overlies an imaging scan head of the probe. In such embodiments, the sheath 202 is configured to inflate with fluid around the imaging scan head to provide a coupling for transmission of ultrasound energy between the imaging scan head and the patient.

Figure 9A:
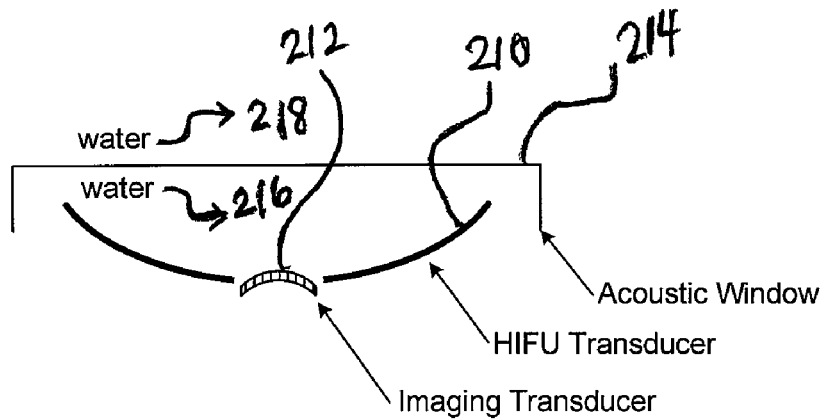
FIGS. 9A-9C illustrate in functional block form a HIFU transducer and imaging transducer behind a common acoustic window or behind separate acoustic windows. Fluid, such as water, is used to fill the space between the transducers and the acoustic window(s) as well as filling the space outside the acoustic window(s) in the body cavity.

FIG. 9A illustrates, in functional block form, a side view of a HIFU transducer 210 and an imaging transducer or scan head 212 disposed behind a common acoustic window 214. In at least one embodiment, the acoustic window 214 may comprise the cover 180 illustrated in FIGS. 7A and 7B. As shown in FIG. 9A, the imaging scan head 212 may be centrally located within the HIFU transducer 210, thus providing an advantageous form factor when fitting the acoustic window 214 to the imaging scan head 212 and transducer 210.

Conventionally, a coupling gel is placed on and around ultrasonic devices, such as the imaging scan head 212 and transducer 210, to improve the acoustic coupling of the devices to the patient. This conventional approach may be acceptable when the ultrasonic devices are pressed against the adjacent tissue to force bubbles out of the coupling gel. However, the global fluid coupling described in the present application allows an imaging scan head 212 (and HIFU transducer 210) to acoustically couple to nearby tissue without requiring direct contact with the tissue. In such cases, if a conventional coupling gel were used to fill the space between the imaging scan head 212 and the acoustic window 214, poor imaging may result from bubbles in the gel that reflect imaging ultrasound energy and cause shadowing in the ultrasound image. Rather than use a coupling gel as is conventionally done, the probe described herein and depicted in FIG. 9A uses a fluid 216, such as water or saline, to fill the space between the imaging scan head 212 and the acoustic window 214. This fluid 216 may be the same as the fluid 218 filling the body cavity.

Figure 9B:
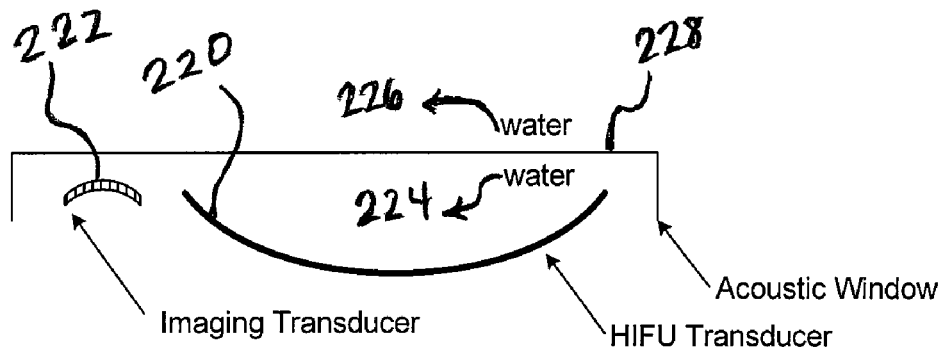

FIG. 9B illustrates, in functional block form, another probe design with a HIFU transducer 220 and an imaging scan head 222. In this embodiment, however, the imaging scan head 222 is located adjacent to the HIFU transducer 220. Like the probe design shown in FIG. 9A, the imaging scan head 222 and the HIFU transducer 220 are behind a common acoustic window 228. A fluid 224, such as water or saline, may be used to fill the space between the imaging scan head 222 and the acoustic window 228. This fluid 224 may be the same as the fluid 226 filling the body cavity.

Figure 9C:
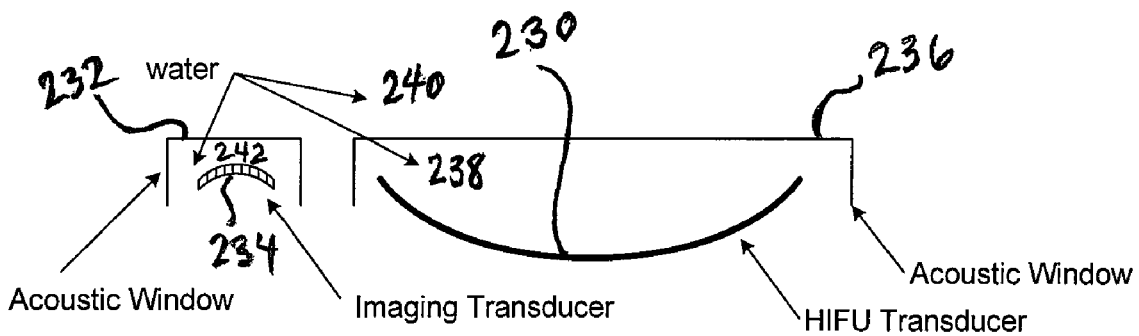

FIG. 9C illustrates, in functional block form, a HIFU transducer 230 and an imaging scan head 234 behind separate acoustic windows 236 and 232, respectively. Fluid 238, 242, such as water or saline, may be used to fill the space between the transducers and the acoustic windows 232, 236. The same or similar fluid 240 may be used to fill the space outside the acoustic windows 232, 236 in the body cavity. The acoustic windows 232, 236 (as well as the acoustic windows 214 and 228 in FIGS. 9A and 9B) may have one or more perforations defined therethrough to allow fluid to flow through the acoustic windows.

Although various embodiments have been described above in connection with certain depicted implementations, those of ordinary skill will recognize that one or more features of any implementation described herein may be combined and used in another implementation for similar advantage. Accordingly, it is not intended that the scope of the invention in any way be limited by the precise forms described above.

The embodiments of the invention in which an exclusive property or privilege is claimed are defined as follows:

1. A combined imaging/high intensity focused ultrasound (HIFU) probe configured for insertion into a body cavity of a patient, comprising:
    an imaging scan head adapted for imaging target tissue in the patient;
    a HIFU transducer having an aperture through which HIFU energy can be transmitted to the target tissue;
    an outlet port configured to direct a flow of fluid from the outlet port across at least a portion of the aperture of the HIFU transducer;
    a first channel in fluid connection with the outlet port for delivering a flow of fluid to the outlet port;
    a cover in sealing engagement with the HIFU transducer, wherein the cover is comprised of a non-permeable material, and wherein the cover has at least one perforation defined therethrough that allows fluid to flow through the cover; and
    an inlet port positioned between the cover and the HIFU transducer, wherein the inlet port is connected to a second channel that conveys fluid away from the HIFU transducer,
    wherein the combined imaging/HIFU probe is configured to allow fluid flow from the outlet port to flow through the at least one perforation in the cover to fill at least a portion of a body cavity with fluid in which the imaging scan head and HIFU transducer are immersed and to direct the fluid flow from the outlet port such that the fluid is capable of flushing an area of tissue in the body cavity near the aperture of the HIFU transducer,
    wherein the outlet port is positioned between the cover and the HIFU transducer such that fluid from the outlet port is configured to flow through the at least one perforation in the cover toward the area in the body cavity near the aperture of the HIFU transducer, the fluid being configured to provide a coupling for transmission of ultrasound energy between the combined imaging/HIFU probe and the patient, and the flushing near the aperture of the HIFU transducer being configured to reduce obstructions to the transmission of HIFU energy, and
    wherein the combined imaging/HIFU probe is configured to draw a higher flow of fluid from the HIFU transducer through the inlet port than the flow of fluid that flows from the HIFU transducer through the at least one perforation in the cover.

2. The combined imaging/HIFU probe of claim 1, wherein the outlet port is positioned proximate to the HIFU transducer.

3. The combined imaging/HIFU probe of claim 1, wherein the outlet port is comprised of a nozzle that directs the fluid flow in a single fluid path toward the area to be flushed.

4. The combined imaging/HIFU probe of claim 3, wherein the outlet port extends around the aperture of the HIFU transducer and directs the fluid flow in a cylindrical or conical-shaped fluid path.

5. The combined imaging/HIFU probe of claim 1, wherein the outlet port is comprised of multiple nozzles that direct the fluid flow in multiple fluid paths toward the area of tissue to be flushed.

6. The combined imaging/HIFU probe of claim 5, wherein the multiple nozzles are positioned in a ring around the aperture of the HIFU transducer.

7. The combined imaging/HIFU probe of claim 1, wherein the fluid flow from the outlet port is continuous.

8. The combined imaging/HIFU probe of claim 1, wherein the probe is further configured to direct the fluid flow from the outlet port to flush an area near the imaging scan head.

9. The combined imaging/HIFU probe of claim 1, wherein the outlet port is a first outlet port, the probe further comprising a second outlet port positioned proximate the imaging scan head to direct a flow of fluid across at least a portion of the imaging scan head, wherein the probe is configured to direct the fluid flow from the second outlet port to flush an area near the imaging scan head and reduce obstructions to the transmission of ultrasound energy between the imaging scan head and the patient.

10. The combined imaging/HIFU probe of claim 1, further comprising a receptacle that uses gravity to deliver fluid, wherein the first channel is configured to receive the flow of fluid from the receptacle.

11. The combined imaging/HIFU probe of claim 1, further comprising a cuff extending around the probe, wherein the cuff is configured to obstruct an opening to the body cavity to help retain fluid from the outlet port in the body cavity.

12. The combined imaging/HIFU probe of claim 11, wherein the cuff is further configured to permit the probe to pivot or translate within the cuff while helping retain the fluid in the body cavity.

13. The combined imaging/HIFU probe of claim 11, wherein the cuff is configured to allow a portion of the fluid filling the body cavity to pass and thereby flow out of the body cavity.

14. The combined imaging/HIFU probe of claim 1, wherein the inlet port is further configured to convey fluid out of the body cavity.

15. The combined imaging/HIFU probe of claim 1, wherein the fluid filling the body cavity has a fluid pressure, the probe further comprising a regulator configured to regulate fluid flow with respect to the body cavity according to a desired pressure of the fluid in the body cavity.

16. The combined imaging/HIFU probe of claim 15, wherein the pressure of the fluid in the body cavity is capable of distending the tissue in the body cavity and modifying the position of the target tissue relative to a focus of the HIFU energy that is transmitted from the HIFU transducer, the regulator being configured to regulate fluid flow with respect to the body cavity to achieve the desired fluid pressure in the body cavity that positions the target tissue at a desired position relative to the focus without moving the position of the HIFU transducer.

17. The combined imaging/HIFU probe of claim 16, wherein the regulator is configured to adjust the fluid flow with respect to the body cavity throughout the transmission of HIFU energy and thereby direct the range of target tissue to be treated by the HIFU energy without moving the position of the HIFU transducer.

18. A combined imaging/high intensity focused ultrasound (HIFU) probe configured for insertion into a body cavity of a patient, comprising:
    an imaging scan head adapted for imaging target tissue in the patient;
    a HIFU transducer having an aperture through which HIFU energy can be transmitted to the target tissue;
    a first channel in fluid connection with an outlet port for delivering a flow of fluid to the body cavity when the probe is inserted into the body cavity;
    a cover in sealing engagement with the HIFU transducer, wherein the cover is comprised of a non-permeable material that has at least one perforation defined therethrough that allows fluid to flow through the cover; and
    an inlet port positioned between the cover and the HIFU transducer, wherein the inlet port is connected to a second channel that conveys fluid away from the HIFU transducer,
    wherein the at least one perforation is positioned in the cover to direct fluid flow through the cover toward an area near the aperture of the HIFU transducer to flush the area of obstructions to the transmission of HIFU energy,
    wherein the combined imaging/HIFU probe is configured to allow fluid flow from the outlet port to flow through the at least one perforation in the cover to fill at least a portion of the body cavity with fluid in which the imaging scan head and HIFU transducer are immersed, the fluid being configured to provide a coupling for transmission of ultrasound energy between the combined imaging/HIFU probe and the patient,
    wherein the outlet port is positioned between the cover and the HIFU transducer such that fluid from the outlet port is configured to flow through the at least one perforation in the cover toward an area in the body cavity near the aperture of the HIFU transducer, and
        wherein the combined imaging/HIFU probe is configured to draw a higher flow of fluid from the HIFU transducer through the inlet port than the flow of fluid that flows from the HIFU transducer through the at least one perforation in the cover.

19. The combined imaging/HIFU probe of claim 18, wherein the cover is further in sealing engagement with the imaging scan head to provide an acoustic window with a fluid-filled space over both the HIFU transducer and the imaging scan head.

20. The combined imaging/HIFU probe of claim 18, wherein the cover is a first cover, the probe further comprising a second cover in sealing engagement with the imaging scan head, wherein the second cover is comprised of a non-permeable material that has at least one perforation defined therethrough to allow fluid to flow through the second cover.

21. A combined imaging/high intensity focused ultrasound (HIFU) probe, comprising:
    an imaging scan head adapted for imaging target tissue in a patient;
    a HIFU transducer having an aperture through which HIFU energy can be transmitted to the target tissue;
    an outlet port configured to deliver a flow of fluid;
    a channel in fluid connection with the outlet port for delivering the flow of fluid;
    a cover in sealing engagement with the HIFU transducer, wherein the cover is comprised of a non-permeable material that has at least one perforation defined therethrough that allows fluid to flow through the cover; and
    a flexible sheath that overlies the cover and is sealingly engaged with the combined imaging/HIFU probe,
    wherein the outlet port is positioned between the cover and the HIFU transducer such that fluid from the outlet port is configured to flow at least in part through the at least one perforation defined in the cover, and
    wherein the combined imaging/HIFU probe is configured to allow fluid flow from the outlet port to fill the space between the HIFU transducer and the cover, and further to flow through the at least one perforation in the cover to fill the space between the cover and the sheath causing the sheath to inflate with fluid, the fluid providing a coupling for transmission of ultrasound energy from the HIFU transducer to the patient.

22. The combined imaging/HIFU probe of claim 21, wherein the fluid is capable of circulating through the space between the aperture of the HIFU transducer and the cover, the probe further comprising an inlet port configured to convey fluid away from the HIFU transducer.

23. The combined imaging/HIFU probe of claim 21, wherein the sheath further extends along a shaft of the probe to cover the shaft.

24. The combined imaging/HIFU probe of claim 21, wherein the sheath further overlies the imaging scan head and is configured to inflate with fluid around the imaging scan head to provide a coupling for transmission of ultrasound energy between the imaging scan head and the patient.

25. A method of deploying a combined imaging/high intensity focused ultrasound (HIFU) probe for use in a body cavity of a patient, comprising:
    inserting the combined imaging/HIFU probe through an opening to the body cavity of the patient, wherein the probe includes:
        an imaging scan head adapted for imaging target tissue in the patient;
        a HIFU transducer having an aperture through which HIFU energy can be transmitted to the target tissue;
        an outlet port configured to direct a flow of fluid from the outlet port across at least a portion of the aperture of the HIFU transducer;
        a first channel in fluid connection with the outlet port for delivering a flow of fluid to the outlet port;
        a cover in sealing engagement with the HIFU transducer, wherein the cover is comprised of a non-permeable material and has at least one perforation defined therethrough that allows fluid to flow through the cover, and wherein the outlet port is positioned between the cover and the HIFU transducer such that fluid from the outlet port is configured to flow through the at least one perforation in the cover toward an area in the body cavity near the aperture of the HIFU transducer; and an inlet port positioned between the cover and the HIFU transducer, wherein the inlet port is connected to a second channel that conveys fluid away from the HIFU transducer;

directing a flow of fluid from the outlet port such that the fluid is capable of flushing the area of tissue in the body cavity near the aperture of the HIFU transducer to reduce obstructions to the transmission of HIFU energy;

allowing fluid flow from the outlet port to flow through the at least one perforation in the cover to fill at least a portion of the body cavity with fluid;

immersing the imaging scan head and HIFU transducer in the fluid in the body cavity, wherein the fluid provides a coupling for transmission of ultrasound energy between the combined imaging/HIFU probe and the patient; and drawing a higher flow of fluid from the HIFU transducer through the inlet port than the flow of fluid that flows from the HIFU transducer through the at least one perforation in the cover.

26. The method of claim 25, further comprising positioning the outlet port proximate to the HIFU transducer.

27. The method of claim 25, wherein the fluid flow is directed in a single fluid path toward the area to be flushed.

28. The method of claim 27, wherein the fluid flow is directed in a cylindrical or conical-shaped fluid path.

29. The method of claim 25, wherein the fluid flow is directed in multiple fluid paths toward the area to be flushed.

30. The method of claim 29, further comprising positioning multiple nozzles in a ring around the aperture of the HIFU transducer to direct the fluid flow.

31. The method of claim 25, wherein the fluid flow from the outlet port is continuous.

32. The method of claim 25, further comprising directing fluid flow from the outlet port toward an area near the imaging scan head to flush the area near the imaging scan head.

33. The method of claim 25, wherein the outlet port is a first outlet port and the probe further includes a second outlet port, the method further comprising directing a flow of fluid from the second outlet port across at least a portion of the imaging scan head to flush an area near the imaging scan head and reduce obstructions to the transmission of ultrasound energy between the imaging scan head and the patient.

34. The method of claim 25, further comprising using gravity to deliver the fluid from a receptacle to the outlet port.

35. The method of claim 25, further comprising positioning a cuff around the probe to obstruct the opening to the body cavity through which the probe is inserted to help retain fluid from the outlet port in the body cavity.

36. The method of claim 35, further comprising pivoting or translating the probe within the cuff while retaining the fluid in the body cavity.

37. The method of claim 35, further comprising allowing a portion of the fluid filling the body cavity to pass by the cuff and thereby flow out of the body cavity.

38. The method of claim 25, further comprising conveying fluid out of the body cavity via the inlet port.

39. The method of claim 25, wherein the fluid filling the body cavity has a fluid pressure, the method further comprising regulating fluid flow with respect to the body cavity according to a desired pressure of the fluid in the body cavity.

40. The method of claim 39, wherein the pressure of the fluid in the body cavity is capable of distending the tissue in the body cavity and modifying the position of the target tissue relative to a focus of the HIFU energy that is transmitted from the HIFU transducer, the method further comprising regulating the fluid flow with respect to the body cavity to achieve the desired fluid pressure in the body cavity that positions the target tissue at a desired position relative to the focus without moving the position of the HIFU transducer.

41. The method of claim 40, further comprising regulating the fluid flow throughout the transmission of HIFU energy and thereby directing the range of target tissue to be treated by the HIFU energy without moving the position of the HIFU transducer.

42. A method of deploying a combined imaging/high intensity focused ultrasound (HIFU) probe for use in a body cavity of a patient, comprising:

inserting the combined imaging/HIFU probe through an opening to the body cavity of the patient, wherein the probe includes:

an imaging scan head adapted for imaging target tissue in the patient;

a HIFU transducer having an aperture through which HIFU energy can be transmitted to the target tissue;

a first channel in fluid connection with an outlet port for delivering a flow of fluid to the body cavity when the probe is inserted into the body cavity;

a cover in sealing engagement with the HIFU transducer, wherein the cover is comprised of a non-permeable material that has at least one perforation defined therethrough that allows fluid to flow through the cover, and wherein the at least one perforation is positioned in the cover to direct fluid flow through the cover toward an area near the aperture of the HIFU transducer to flush the area of obstructions to the transmission of HIFU energy; and an inlet port positioned between the cover and the HIFU transducer, wherein the inlet port is connected to a second channel that conveys fluid away from the HIFU transducer, wherein the outlet port is positioned between the cover and the HIFU transducer such that fluid from the outlet port is configured to flow through the at least one perforation in the cover toward an area in the body cavity near the aperture of the HIFU transducer;

allowing fluid flow from the outlet port to flow through the at least one perforation in the cover to fill at least a portion of the body cavity with fluid;

immersing the imaging scan head and HIFU transducer in the fluid in the body cavity, wherein the fluid provides a coupling for transmission of ultrasound energy between the combined imaging/HIFU probe and the patient; and drawing a higher flow of fluid from the HIFU transducer through the inlet port than the flow of fluid that flows from the HIFU transducer through the at least one perforation in the cover.

43. The method of claim 42, further comprising conveying fluid out of the body cavity via the inlet port.

44. The method of claim 42, further comprising covering the imaging scan head with the cover, wherein the cover is in sealing engagement with both the HIFU transducer and the imaging scan head to provide an acoustic window with a fluid-filled space over both the HIFU transducer and the imaging scan head.

45. The method of claim 42, wherein the cover is a first cover, the method further comprising covering the imaging scan head with a second cover, wherein the second cover is comprised of a non-permeable material in sealing engagement with the imaging scan head that has at least one perforation defined therethrough to allow fluid to flow through the second cover.

46. A method of deploying a combined imaging/high intensity focused ultrasound (HIFU) probe for use in a body cavity of a patient, comprising:

inserting the combined imaging/HIFU probe through an opening to the body cavity of the patient, wherein the probe includes:
  an imaging scan head adapted for imaging target tissue in a patient;
  a HIFU transducer having an aperture through which HIFU energy can be transmitted to the target tissue;
  an outlet port configured to deliver a flow of fluid;
  a channel in fluid connection with the outlet port for delivering the flow of fluid; and
  a cover in sealing engagement with the HIFU transducer, wherein the cover is comprised of a non-permeable material that has at least one perforation defined therethrough that allows fluid to flow through the cover,
  wherein the outlet port is positioned between the cover and the HIFU transducer such that fluid from the outlet port is configured to flow at least in part through the at least one perforation defined in the cover;
covering the combined imaging/HIFU probe with a flexible sheath that overlies the cover and is sealingly engaged with the combined imaging/HIFU probe; and
allowing fluid flow from the outlet port to fill the space between the HIFU transducer and the cover, and further to flow through the at least one perforation in the cover to fill the space between the cover and the sheath causing the sheath to inflate with fluid, wherein the fluid provides a coupling for transmission of ultrasound energy from the HIFU transducer to the patient.

47. The method of claim 46, wherein the combined imaging/HIFU probe further includes an inlet port and the fluid is capable of circulating through the space between the aperture of the HIFU transducer and the cover, the method further comprising conveying fluid away from the HIFU transducer via the inlet port.

48. The method of claim 46, wherein the combined imaging/HIFU probe further includes an inlet port and the fluid is capable of circulating through the space between the aperture of the HIFU transducer and the cover, the method further comprising conveying fluid away from the HIFU transducer via the inlet port.

49. The method of claim 46, wherein covering the combined imaging/HIFU probe with a flexible sheath further includes causing the sheath to overlie the imaging scan head and inflate with fluid around the imaging scan head to provide a coupling for transmission of ultrasound energy between the imaging scan head and the patient.

* * * * *

UNITED STATES PATENT AND TRADEMARK OFFICE
CERTIFICATE OF CORRECTION

| | | Page 1 of 1 |
|---|---|---|
| PATENT NO. | : 8,052,604 B2 | |
| APPLICATION NO. | : 11/831048 | |
| DATED | : November 8, 2011 | |
| INVENTOR(S) | : Lau et al. | |

It is certified that error appears in the above-identified patent and that said Letters Patent is hereby corrected as shown below:

| COLUMN | LINE | ERROR |
|---|---|---|
| 20 (Claim 20, | 19 line 18) | "theat" should read --the at-- |
| 24 (Claim 48, | 12-17 lines 1-5) | Delete the entire text of Claim 48, and insert therefor --The method of Claim 46, wherein the sheath further extends along a shaft of the probe to cover the shaft.-- |

Signed and Sealed this
Thirty-first Day of July, 2012

David J. Kappos
*Director of the United States Patent and Trademark Office*